(12) United States Patent
Taylor et al.

(10) Patent No.: US 8,247,541 B2
(45) Date of Patent: Aug. 21, 2012

(54) PLANT COMPOSITIONS ENRICHED IN DEHYDROSOYASAPONIN I (D-I) AND METHODS OF PRODUCING SUCH COMPOSITIONS

(75) Inventors: Wesley G Taylor, Saskatoon (CA); Ken W Richards, Saskatoon (CA)

(73) Assignee: Her Majesty the Queen in right of Canada, as represented by the Minister of Agriculture and Agri-Food, Saskatoon, Saskatchewan (CA)

( * ) Notice: Subject to any disclaimer, the term of this patent is extended or adjusted under 35 U.S.C. 154(b) by 340 days.

(21) Appl. No.: 12/522,436

(22) PCT Filed: Dec. 14, 2007

(86) PCT No.: PCT/CA2007/002272
§ 371 (c)(1),
(2), (4) Date: Nov. 4, 2009

(87) PCT Pub. No.: WO2008/083461
PCT Pub. Date: Jul. 17, 2008

(65) Prior Publication Data
US 2010/0056470 A1     Mar. 4, 2010

Related U.S. Application Data

(60) Provisional application No. 60/879,230, filed on Jan. 8, 2007.

(51) Int. Cl.
*C07G 3/00* (2006.01)
*C07H 17/00* (2006.01)
*C07H 1/06* (2006.01)
*C07H 1/08* (2006.01)

(52) U.S. Cl. ...................... 536/18.5; 536/128
(58) Field of Classification Search ................. None
See application file for complete search history.

(56) References Cited

U.S. PATENT DOCUMENTS

| 5,955,082 A | 9/1999 | Bodnaryk |
| 2006/0216367 A1 | 9/2006 | Taylor |

FOREIGN PATENT DOCUMENTS

CA        2546138 A1 * 11/2006

OTHER PUBLICATIONS

Kerem et al. J Sci Food Agric 85: 406-412, 2005.*
Jood et al. J. Sci. Food Agric. 1986, 37, 1121-1124.*
Saskatchewan Pulse Growers, Pulse Production Manual 2000, Variety Selection 3.1.*
Anderson et al. J Nutr. Mar. 1995; 125(3 Suppl): 581S-588S.*
Gurfinkel, D. M. et al., "The isolation of soyasaponins by fractional precipitation, solid phase extraction, and low pressure liquid chromatography." Int. J. Food Sci. Nutr. 56(7):501-519, 2005.
Taylor, W. G. et al., "Insecticidal Components from Field Pea Extracts: Soyasaponins and Lysolecithins." J. Agric. Food Chem. 52(25):7484-7490, 2004.

* cited by examiner

*Primary Examiner* — Layla Bland
(74) *Attorney, Agent, or Firm* — Nixon Peabody LLP

(57) ABSTRACT

There is provided a method of producing a plant composition comprising dehydrosoyasaponin I (D-I), the method comprising the steps of extracting a plant flour with a solvent capable of extracting soyasaponins to produce an extract, and treating the extract with light. Also provided are compositions produced according to the method of the present invention.

18 Claims, 9 Drawing Sheets

2-butylfuran (2-bf)

4,5-dihydro-3,4-dihydroxy-3-methyl-
2(3H)-furanone (4,5-df)

5,7-dihydroxy-4'-methoxyisoflavone 7-O-β-
D-glucopyranoside (sissotrin)

6'-malonyltrifolirhizin (6-mt)

kaempferol 3-O-β-D-apiofuranosyl-
(1 → 2)-β-D-glucopyranoside (kag)

kaempferol 3-O-β-D-apiofuranosyl-
(1 → 3)-6-O-malonyl-β-D-glucopyranoside (kamg)

PLANT COMPOSITIONS ENRICHED IN DEHYDROSOYASAPONIN I (D-I) AND METHODS OF PRODUCING SUCH COMPOSITIONS

CROSS REFERENCE TO RELATED APPLICATIONS

This application is a 371 National Phase Entry Application of co-pending International Application PCT/CA2007/002272 filed Dec. 14, 2007, which designated the U.S., and claims the benefit under 35 U.S.C. 119(e) of U.S. Provisional Application Ser. No. 60/879,230 filed on Jan. 8, 2007 the contents of which are incorporated herein by reference in their entirety.

FIELD OF INVENTION

The present invention relates to plant compositions comprising soyasaponins. More specifically, the present invention relates to plant compositions comprising dehydrosoyasaponin I (D-I) and methods of producing such compositions.

BACKGROUND OF THE INVENTION

Triterpenoid saponins are widely distributed in legume crops (9, 52). For example, soybean seeds contain on a dry weight basis about 0.5% of types A and B soyasaponins, depending on variety, cultivation year, location of growth and degree of maturity (55). The main saponins of soybeans (more than 20 have been identified) are glycosides of soyasapogenol B, the aglycone of soyasaponin I (S-I). Although S-I was initially thought to be the principal ingredient, it is currently believed that S-I does not exist as a free alcohol (C-22 OH) in soybeans but is formed during extraction from the naturally-occurring soyasaponin VI (S-VI), also known as soyasaponin βg, soyasaponin BeA or chromosaponin I (35, 40). The hydrolytic reaction occurring at C-22, generating 3-hydroxy-2-methyl-4-pyrone (maltol) and S-I, is reputed to occur gradually in solution, is promoted by heat and is catalyzed by alkaline conditions. This type of conjugation has been demonstrated to occur in other legumes, including pea seedlings (*Pisum sativum* L.) and mature chickpea (*Cicer arietinum* L.) seeds (29, 65). In 1996, levels of S-VI in two cultivars of chickpea were estimated at 0.075% (desi type) and 0.071% (kabuli type) on a dry weight basis (53). Earlier, a sample of chickpea was reported to possess levels of soyasapogenol B of 0.075% (24). Varietal differences and effects of processing on saponin content of chickpea have also been studied (27). The biological and pharmacological activities of saponins have been reviewed (36).

Although field peas were initially thought to contain S-I (and then S-VI) as the only soyasaponin, we recently showed that field pea extracts contained dehydrosoyasaponin I (D-I) as a minor component. D-I isolated in small quantities from pea had insecticidal and antifeedant properties against stored product insect pests (59, 60, 61). This C-22 keto saponin, with soyasapogenol E as the aglycone, had also been isolated as a minor component from immature green pea seeds (45). D-I was also known to occur as a minor component in soybeans (35) and other legume species (8, 30, 32-34, 41, 43, 44, 70) but not in chickpea. D-I isolated from leaves of *Desmodium adscendens* was shown to be a high-affinity activator of calcium-dependent potassium channels and was 60 fold more potent than S-I as a potassium channel opener (41, 42, 46). The occurrence of D-I in leaves of *D. adscendens*, a popular herbal medicine used in some countries such as Ghana, might explain the medicinal value of this herb as a treatment for asthma and other conditions associated with smooth muscle contraction (1). Since the concentration of D-I in all known sources was very low, better sources of D-I are needed to explore its medicinal value.

We have shown here that aqueous alcohol extracts from the chickpea (*Cicer arietinum* L.) were capable of yielding a rare but highly valuable triterpenoid saponin dehydrosoyasaponin I (D-I) in relatively high yields. D-I is a valuable natural product because it is known to be a potent calcium-activated potassium channel opener (41). Agents that modulate potassium channels are emerging therapeutic drug targets for treating cardiovascular, urological, respiratory, neurological and other disorders (38, 46, 47). The development of D-I for these and other medicinal applications has been severely hampered because an adequate supply of D-I has not been available. Thus, there is a need in the art for plant compositions enriched in dehydrosoyasaponin I (D-I) and also novel methods of producing compositions enriched in dehydrosoyasaponin I (D-I). Further, there is also a need in the art for novel methods of producing other soyasaponins, for example S-I as described herein.

SUMMARY OF THE INVENTION

The present invention relates to plant compositions comprising soyasaponins. More specifically, the present invention relates to plant compositions comprising dehydrosoyasaponin I (D-I) and methods of producing such compositions.

According to the present invention there is provided a method of producing a plant composition comprising dehydrosoyasaponin I (D-I), the method comprising, a) extracting a plant flour with a soyasaponin extracting solvent to produce an extract, and;

b) treating the extract with light.

Also provided by the present invention is a method as defined above wherein the extracting further comprises, or is preceded by a step of processing a plant or part thereof to produce a flour.

Also provided by the present invention is a method as defined above, wherein the plant flour comprises fermented seed and/or fermented seed flour.

The present invention also provides the method as defined above, wherein the plant flour comprises dehydrosoyasaponin I (D-I), soyasaponin VI (S-VI) or both.

The present invention also provides a method as defined above and further comprises one or more steps of purifying dehydrosoyasaponin I (D-I) from the extract treated with light.

Also provided by the present invention is the method as defined above, wherein the plant flour is derived from a legume, for example, but not limited to one or more of soybean (*Glycine max*), field pea (*Pisum sativum*), chickpea (*Cicer arietinum*), lentil (*Lens culinaris*), alfalfa (*Medicago sativa*), American groundnut (*Apios americana*), scarlet runner beans (*Phaseolus coccineus*), blue or narrow leafed lupin (*Lupinus angustifolius*), hyacinth bean (*Dolichos lablab*), black bean (*Vigna mungo*), adzuki or azuki bean (*Vigna angularis*, synonymous with *Phaseolus angularis*), *Desmodium styracifolium*, *Wistaria brachybotrys*, *Sophora subprostrata*, *Desmodium adscendens*, *Lupinus polyphyllus*, *Lupinus arboreus*, *Trifolium alexandrinum*, *Abrus cantoniensis*, or *Phaseolus vulgaris*.

The present invention also contemplates a method as defined above, wherein the plant flour is from plant seed, the plant seed comprising soyasaponin VI (S-VI). In an embodiment, which is not meant to be limiting in any manner, the seed is chickpea seed, for example, but not limited to, chickpea seed from CDC Anna, CDC Cabri, CDC Desiray, CDC Nika, Myles, Amit, CDC ChiChi, CDC Chico, CDC Diva, CDC Frontier, CDC Verano, CDC Xena, CDC Yuma, Dwelley, Sanford or a combination thereof. In an alternate non-limiting embodiment, the chickpea seed is Amit. However, any plant or part thereof which comprises soyasaponin VI (S-VI) may be employed in the methods as described herein. Preferably, the any plant or part thereof is a plant flour, more preferably a plant seed flour. In still a more preferable embodiment, the plant flour is a plant seed flour comprising soyasaponin S-VI and a photosensitizer, for example, but not limited to riboflavin.

Also provided by the present invention, is a method as defined above, wherein the step of processing comprises grinding, milling, pulverizing, crushing, pressing, or pounding the plant or part thereof to produce a flour that comprises a meal or powder.

The present invention also provides a method as described above wherein the soyasaponin extracting solvent is an alcohol-based solvent. Preferably, the alcohol-based solvent is an aqueous alcohol comprising ethanol and water or methanol and water. In an embodiment of the present invention the aqueous alcohol solvent comprises from about 10:90 to about 90:10 alcohol:water. It is also contemplated that the solvent may be acidic, for example, but not wishing to be bound by theory or limiting in any manner, to liberate factors that may enhance the conversion of soyasaponin VI (S-VI) to dehydrosoyasaponin (D-I).

In a further embodiment, it is also contemplated that the soyasaponin extracting solvent may comprise a buffered solvent, for example, but not limited to an acidic buffered solvent. Further, it is also contemplated that the soyasaponin extracting solvent may comprise one or more enzymes, for example, but without limitation, one or more hydrolytic enzymes to facilitate extraction of soyasaponins, photosensitizers or both Also contemplated by the present invention is a method as described above, wherein the treating comprises illumination with light including, but not limited to fluorescent and/or incandescent light, UVA, UVB, UVC or a combination thereof for a period of from about 1 day to about 7 days. Preferably, the light is in the visible range at an intensity less than about 8000 lux, more preferably between about 2000 and 2500 lux.

The present invention also provides a method as described above, wherein the step of extracting and treating are performed concurrently.

The present invention also provides a method of producing a plant composition comprising dehydrosoyasaponin I (D-I), the method comprising,
a) providing a plant flour, or
   processing the plant or part thereof to produce a composition comprising a flour;
b) extracting the flour with a soyasaponin extracting solvent to produce an extract, and;
c) treating the extract with light.

The present invention also provides a method as described above, wherein two or more of the steps of providing, processing, extracting and treating are practiced concurrently.

Also provided by the present invention is a plant composition comprising dehydrosoyasaponin I (D-I) produced by a method as described above.

The present invention also provides a composition as described above, wherein the composition comprises a D-I to soyasaponin ratio (D-I/(D-I+S-I+S-VI)) of from about 0.05 to about 0.9 or higher. In an embodiment, the composition comprises dehydrosoyasaponin I (D-I), and at least one of soyasaponin I (S-I), soyasaponin-VI (S-VI), or both. In a further embodiment, the composition comprises dehydrosoyasaponin I (D-I), soyasaponin I (S-I), and soyasaponin-VI (S-VI).

The present invention also provides a plant composition comprising,
a) dehydrosoyasaponin I (D-I), soyasaponin I (S-I) and soyasaponin VI (S-VI), and;
b) a D-I to soyasaponin ratio (D-I/(D-I+S-I+S-VI)) of about more than about 0.05 to about 0.9 or higher.

In a preferred embodiment, which is not meant to be limiting, the composition is a chickpea seed extract.

The present invention also provides a method of producing dehydrosoyasaponin I (D-I) from soyasaponin VI (S-VD) comprising the steps of adding a photosensitizer selected from the group consisting of riboflavin, FAD, FMN or a combination thereof to the soyasaponin VI (S-VI) and then treating the resulting composition with light. Also, the present invention contemplates a method of producing dehydrosoyasaponin I (D-I) from soyasaponin VI (S-VI) comprising the steps of adding to the soyasaponin VI (S-VI) a soyasaponin extract comprising free photosensitizer derived from a plant flour treated with a soyasaponin extracting solvent, and then treating the resulting composition with light.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
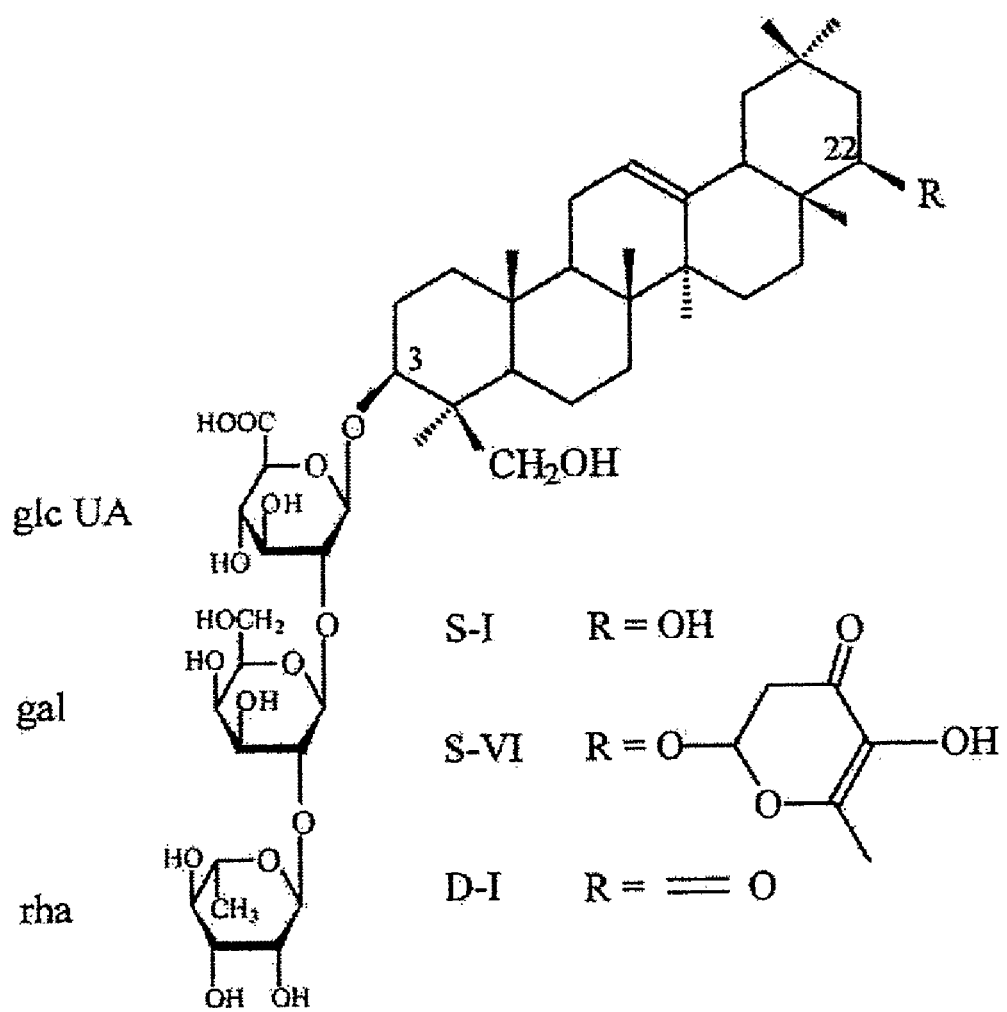
FIG. 1 shows structures of the soyasaponins identified in chickpea extracts. S-I, soyasaponin I; D-I, dehydrosoyasaponin I; S-VI, soyasaponin VI.

The following description is of a preferred embodiment. Methods of Producing Plant Compositions Comprising Dehydrosoyasaponin I (D-I)

The present invention provides a method of producing a plant composition comprising dehydrosoyasaponin I (D-I), the method comprising, a) extracting a plant flour with a suitable solvent to produce an extract, and;

b) treating the extract with light.

In a further embodiment of the method as described above, the invention provides a method of producing a plant composition comprising dehydrosoyasaponin I (D-I), the method comprising, a) providing a plant flour, or
processing the plant or part thereof to produce a composition comprising a flour;

b) extracting the flour with a suitable solvent to produce an extract, and;

c) treating the extract with light.

The plant processed according to the method of the present invention may comprise any plant or part thereof which produces or is capable of producing dehydrosoyasaponin I (D-I) and/or soyasaponin VI (S-VI). As suggested by the results provided herein, but without wishing to be bound by theory or limiting in any manner, the production of dehydrosoyasaponin I (D-I) by the action of light is accompanied by a reduction in the level of soyasaponin VI (S-VI) which suggests that dehydrosoyasaponin I (D-I) could be a photoproduct of soyasaponin VI (S-VI). Accordingly, any plant or part thereof, plant composition or plant flour which comprises dehydrosoyasaponin I (D-I), soyasaponin VI (S-VI) or both may be employed in the method of the present invention. Nonlimiting examples of such plants include legumes such as soybeans (*Glycine max*), field pea (*Pisum sativum*), chickpea (*Cicer arietinum*), lentil (*Lens culinaris*), alfalfa (*Medicago sativa*), American groundnut (*Apios americana*), scarlet runner beans (*Phaseolus coccineus*), blue or narrow leafed lupin (*Lupinus angustifolius*), hyacinth bean (*Dolichos lablab*), black bean (*Vigna mungo*), adzuki or azuki bean (*Vigna angularis*, synonymous with *Phaseolus angularis*), one or more *Desmodium* species, for example, but not limited to *Desmodium styracifolium* and *Desmodium adscendens, Wistaria brachybotrys, Sophora subprostrata, Lupinus polyphyllus, Lupinus arboreus, Trifolium alexandrinum, Abrus cantoniensis*, or *Phaseolus vulgaris*. In a preferred embodiment, plant seed is employed in the methods as provided herein.

In an embodiment of the present invention, which is not meant to be considered limiting in any manner, the plant, part thereof or plant composition comprising a flour is derived from chickpea, soybean or field pea. In a preferred embodiment, it is derived from a chickpea plant. Any variety of chickpea plant may be employed in the method of the present invention, including kabuli and/or desi chickpeas, for example, but not limited to varieties such as CDC Anna, CDC Cabri, CDC Desiray, CDC Nika, Myles, Amit, CDC ChiChi, CDC Chico, CDC Diva, CDC Frontier, CDC Verano, CDC Xena, CDC Yuma, Dwelley, and Sanford. Varieties of Amit are particularly preferred as such varieties are capable of producing relatively large amounts of dehydrosoyasaponin I (D-I) when treated with light, as provided by the method of the present invention.

In a preferred embodiment, the step of providing a flour or processing a plant or part thereof to produce a composition comprising a flour employs the seed of the plant to produce the flour. However, it is also contemplated that other parts of the plant may be used to practice the method of the present invention, including but not limited to the whole plant, stems, knots, roots, leaves, branches, flowers, seedlings or any combination thereof.

By the terms "processing the plant or part thereof" it is meant subjecting the whole plant, or any part or combination of parts thereof to a disruption process, for example, but not limited to a physical disruption process such as grinding, milling, pulverizing, crushing, pressing, pounding or a combination thereof to produce a composition of particles, meal or powder that is termed "flour". In a preferred embodiment, the flour is obtained from seed. However, as it is known the dehydrosoyasaponin I (D-I) and/or soyasaponin VI (S-VI) may be obtained from whole plants or various parts thereof, it is also contemplated that parts of the plant other than seed may be used to practice the method of the present invention, including but not limited to the whole plant, knots, roots, leaves, stems, branches, flowers, seedlings or any combination thereof.

As will be evident to a person of skill in the art, the production of plant flour may be accomplished by a variety of methods as known in the art. Further, such methods may employ one or more devices or apparatuses known in the art, including, but not limited to a Wiley mill, Thomas mill, Cyclotech mill, jet mill, centrifugal mill, pin mill with or without air classification, or any combination thereof.

It is also contemplated that the flour may be further processed to comprise one or more additional characteristics. For example, the flour may be defatted with chloroform or other appropriate solvent, dried to a particular moisture content or range, or the flour may be sifted or sized by passing through a mesh screen or the like to obtain compositions having a desired particle size, size range or size distribution. It is also contemplated that seeds employed to produce flour may be subject to one or more pretreatments, for example, but not limited to dehulling, fermenting or both. Other pretreatments or processing conditions, for example, but not limited to dry processing or wet processing as would be known by a person of skill in the art also may be employed in the method of the present invention.

Generally, flour comprising smaller particles is preferred to facilitate extraction of soyasaponin components. Without wishing to be limiting, the step of processing may be performed to produce a flour that passes through a screen, preferably comprising a size of between about 40 mesh to about 200 mesh or more, for example, 40, 50, 60, 70, 80, 90, 100, 110, 120, 130, 140, 150, 160, 170, 180, 190, 200 mesh or any value therein between. Further, the flour may be characterized as passing through a mesh size defined by any two of the values listed above.

By the terms "extracting the flour" it is meant contacting the plant, part thereof or flour processed from the plant with a suitable solvent (i.e. a soyasaponin extracting solvent) meaning that it is capable of extracting soyasaponins including, for example, but not limited to dehydrosoyasaponin I (D-I), soyasaponin I (S-I) and soyasaponin VI (S-VI) from the plant, part thereof or flour into the solvent. In a preferred embodiment, the solvent is an alcohol-based solvent meaning that the solvent comprises alcohol. The alcohol of the alcohol-based solvent is preferably a low molecular weight alcohol, such as methanol, ethanol, n-propanol, isopropanol, 2-propen-1-ol (allyl alcohol), n-butanol, tert-butanol, 1-isobutanol, 2-buten-1-ol (crotyl alcohol), tert-pentanol or a mixture thereof. More preferably, the flour is extracted with an aqueous alcohol-based solvent comprising an alcohol of 1 to 4 carbons and water, for example ethanol/water or methanol/water. In the event that the alcohol-based solvent comprises ethanol/water, the amount per volume of ethanol to water is preferably in the range of about 25/75 (ethanol/water) to about 75/25 (ethanol/water), more preferably about 50/50 (ethanol/water). In the event that the alcohol-based solvent comprises methanol/water, the amount per volume of methanol to water is preferably in the range of about 70/30 methanol/water to about 80/20 methanol/water, preferably about 75/25 (methanol/water). As will be evident to a person of skill in the art, other combinations of methanol/water, ethanol/water or other solvents or combinations of solvents may be employed in the method of the present invention.

The temperature of extraction or the temperature of the alcohol-based solvent employed in the extraction is not critical to the present invention and may be at room temperature, for example, a temperature of about 17-22 degrees C. or a temperature above or below room temperature. Further, as provided in the examples, the extraction may be performed under reflux. Persons skilled in the art will recognize advantages to employing elevated or low temperatures for extraction. For example, increasing alcohol above room temperature, such as a range from about 40 to 85 degrees C., may shorten the time of an extraction step.

It is also contemplated that the step of extracting may be performed at elevated pressures and temperatures. For example, but not wishing to be considered limiting in any manner, the method may employ subcritical water extraction to extract soyasaponins as would be understood a person of skill in the art. In such an embodiment, water may be employed as the soyasaponin extracting solvent.

By the terms "treating the extract with light" it is meant irradiating the extract with light for a period of time sufficient to increase the amount of dehydrosoyasaponin I (D-I) in the extract. Without wishing to be considered limiting in any manner, the extract may be irradiated with light in the visible range from a standard fluorescent or incandescent bulb, Alternatively, the extract may be irradiated with visible light, fluorescent light, sunlight, light in the UVA, UVB, UVC range, or any combination thereof. Extracts also may be irradiated with sunlight alone or in addition to one or more other types of light as described herein. In a preferred embodiment, the extract is subjected to a light intensity of less than 8000 lux, preferably about 500 lux to 7000 lux, more preferably about 2000 lux to about 2500 lux. However, the present invention contemplates subjecting the extracts to light with an intensity of about 100, 200, 300, 400, 500, 600, 700, 800, 900, 1000, 1500, 2000, 2500, 3000, 3500, 4000, 4500, 5000, 5500, 6000, 6500, 7000, 7500, 8000 lux. Further, the extracts may be subjected to a range of light intensities defined by any two of the values provided above.

In an embodiment of the present invention, but not wishing to be limiting in any manner, the extract comprises a solvent which may or may not be the same as the solvent for extracting the soyasaponins. For example, it is contemplated that the extract may be performed in an ethanol/water solvent, but that the step of treating with light may be performed in a methanol/water solvent or vice versa. However, it is generally preferred that the step of extracting and the step of treating is performed in the same solvent. In a preferred embodiment, the extract comprising solvent is treated with light for a period between about 0.5 hrs and 7 days, for example 0.5 hrs, 1, 2, 5, 10, 15, 20, 24 hours, 1 day, 2, 3, 4, 5, 6, 7 days or any time period therein between. However, the duration of the treatment may be dependent on various factors including, but not limited to the intensity of the light used to irradiate the extract, the concentration of the extract, the temperature of the extract solvent, the path length of the light through the extract, and other factors that would be known to a person of skill in the art.

It is to be understood that the method of the present invention or any step described therein may further comprise one or more additional processing steps. Such steps may include without limitation drying, concentrating, filtering, purifying, analyzing, quantifying or any combination thereof. For example, but not to be considered limiting in any manner, the extract obtained from extracting the flour and after treating with light may be subjected to a form of chromatography or treatment with nonionic macroreticular resin such as, but not limited to Diaion HP-20 or the like. However, such treatments or additional purification steps are not required in order to obtain extracts enriched in dehydrosoyasaponin I (D-I) as provided by the method of the present invention.

It is also contemplated that the extract resulting from extraction with an alcohol-based solvent may be further characterized and components therein may be quantified and/or purified by one or more methods known in the art, for example, but not limited to HPLC, thin layer chromatography, mass spectrometry, NMR spectroscopy or a combination thereof.

It is also contemplated that the steps of processing, extracting and treating, as defined by the method of the present invention may be practiced as distinct steps or any two or all three of the steps may be practiced concurrently. For example, but not wishing to be considered limiting, the plant or part thereof may be processed in the presence of a solvent capable of extracting soyasaponins to produce the extract. In such an embodiment, it is preferred that the plant or part thereof is processed by physical, chemical or mechanical means as would be known in the art to produce particles in the solvent which would resemble a powder, meal or flour if the solvent was removed therefrom and the resulting composition comprising the particles was dried. In a further embodiment, but without wishing to be considered limiting in any manner, it is possible that the flour may be extracted with solvent and treated with light at the same time. In yet a further embodiment, but without wishing to be limiting in any manner, a plant or portion thereof may be processed, extracted with solvent and treated with light all at the same time. Other variations are also possible as would be understood by a person of skill in the art having the teachings as provided herein.

The results provided in the tables and examples herein demonstrate that compositions comprising dehydrosoyasaponin I (D-I) can be produced from various plants by treating extracts therefrom with light. The results also suggest that some type of plants produce more dehydrosoyasaponin I (D-I) than others. Without wishing to be bound by theory or limiting in any manner, it is possible that select types or varieties of plants may contain an unknown factor which catalyses or aids in the production of D-I in those plants. Accordingly, the present invention also contemplates a method of producing a plant composition comprising dehydrosoyasaponin I (D-I) wherein an extract from a plant capable of producing D-I upon treatment with light is added to a second plant extract that comprises soyasaponin VI (S-VI) and the second plant extract is treated with light. In such an embodiment, preferably the extract from a plant capable of producing D-I is chickpea seed from field grown Amit.

The present invention also provides a method of producing dehydrosoyasaponin I (D-I) from soyasaponin VI (S-VI) comprising the steps of adding a photosensitizer selected from the group consisting of riboflavin, FAD, FMN, or a combination thereof, a soyasaponin extract from a plant flour treated with a soyasaponin extracting solvent, or any combination or sub-combination thereof, to produce a composition comprising soyasaponin VI (S-VI) and treating the resulting composition comprising soyasaponin VI (S-VI) with light.

In an a preferred embodiment wherein a photosensitizer is added, preferably the photosensitizer is added in an amount between about 1 M and about 10 µM, for example 1 nM, 10 nM, 50 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM or 10 µM, more preferably between about 1 µM and about 10 µM of the total composition. In an alternate embodiment, which is not meant to be limiting in any manner, the soyasaponin extract that is added comprises a extract that shows good conversion of S-VI to D-I itself when treated with light, for example such as extracts of Amit and others as provided herein. Other photosensitizers also may be added, alone or in combination with those provided herein to effect conversion of soyasaponin IV (S-IV) to dehydrosoyasaponin D-I.

Plant Compositions/Extracts comprising Dehydrosoyasaponin I (D-I)

The present invention also comprises a plant composition or extract produced according to the method of the present invention as described above. In a preferred embodiment, there is provided a plant extract produced according to the method as described above. In still a further embodiment, there is provided a plant seed extract, more preferably a chickpea seed extract, even more preferably an Amit chickpea extract produced by the method of the present invention. As shown herein, the treatment of extracts with light alters the natural levels of soyasaponins, increases the level of dehydrosoyasaponin I (D-I) in the compositions and changes the levels of other soyasaponins, for example, but not wishing to be limiting, soyasaponin VI (S-VI). Thus, by altering the levels of one or more soyasaponins in the composition, the compositions obtained after treatment with light are distinctly different from the compositions of the plants that have been described in the art, or that exist in nature.

The plant compositions or extracts may be characterized as comprising dehydrosoyasaponin I (D-I) alone or in combination with soyasaponin S-VI (S-VI), soyasaponin I (S-I), or both. Other components also may be present in the extract including, without limitation, proteins, peptides, carbohydrates, oligosaccharides, lipids, phospholipids, fatty acids, alkaloids, flavonoids, and saponins other than D-I, S-I and S-VI, as described herein and throughout. However, one or more of such other components may be absent from the plant compositions. Further, the plant compositions or extracts also may be characterized as comprising a D-I to soyasaponin ratio (D-I/(D-I+S-I+S-VI)) of more than about 0.05, preferably more than about 0.10, 0.15, 0.20, 0.30, 0.35, 0.40, 0.45, 0.50, 0.55, 0.60, 0.65, 0.70, 0.75, 0.8, 0.85, 0.9, 0.95 or higher, or any amount therein between. Further, the compositions or extracts may be characterized by a range of ratios from about 0.1 to about 0.9, about 0.2 to about 0.9, about 0.3 to about 0.9, about 0.4 to about 0.9, about 0.5 to about 0.9 and the like. The ratio is calculated by dividing the amount of dehydrosoyasaponin I (D-I) by the sum of dehydrosoyasaponin I (D-I), soyasaponin I (S-I) and soyasaponin VI (S-VI). The amounts of each soyasaponin may be determined or estimated by an appropriate method known in the art. For example, but not to be considered limiting in any manner, the ratio may be calculated from the peak areas of each soyasaponin as determined by HPLC or the like, even though the exact amount of each soyasaponin may be unknown. Variations of such a technique, for example, including an internal reference standard or compound of known concentration can provide further information as would be understood by a person of skill in the art and may be employed to characterize the compositions of the present invention.

In addition to the D-I to soyasaponin ratio, the compositions and extracts of the present invention may further comprise other characteristics. For example, but not to be considered limiting, the total amount of soyasaponins (D-I, S-I and S-VI) may be greater than a defined amount or within a range of defined amounts. In such a case, a composition comprising a large D-I to soyasaponin ratio, and a large total amount of soyasaponin would contain a large amount of D-I.

Although it is preferred to characterize the compositions of the present invention in terms of the D-I to soyasaponin ratio (D-I/(D-I+S-I+S-VI)), the compositions also may be characterized as comprising a D-I index, or a D-I purity index above a specified amount or within a range of amounts. A D-I index from HPLC/ELSD ratios was used to compare extracts from the same desi and kabuli varieties, but with extracts obtained under brief and 7-day laboratory exposure to light. The rankings at 7-days were similar to before (1-4 days of light exposure), with Amit and CDC ChiChi leading other chickpea varieties and displaying D-I indexes of 38-50 and 11-14 respectively. Importantly, a commercial sample of Amit from Saskatchewan gave a D-I index of 34. Desi varieties of CDC Cabri and Myles gave 7-day D-I indexes of 7.3 and 5.0, which were comparable to those of CDC Verano (7.5), CDC Chico (6.6), CDC Yuma (6.6), Sanford (4.1) and Frontier (3.3). Accordingly, the present invention contemplates a composition or extract comprising a D-I index of greater than 1, more preferably greater than 2, 3, 4, 5, 6, 7, 8, 9, 10, 12, 15, 17, 20, 22, 25, 30, 35, 40, 45, 50 or more.

Without wishing to be bound by theory or limiting in any manner, a genetic (or variety) component may be important, not necessarily for D-I itself, but rather for a co-extracted factor that enhances the photoconversion to D-I (probably the photoconversion of S-VI to D-I). With brief (minimal) exposure to light, levels of D-I were low (D-I index for Amit of about 1.5-2.5) or very low (D-I index for other varieties of less than about 1).

The results provided in the Examples, Tables and disclosure throughout demonstrate that dehydrosoyasaponin I (D-I) may be isolated from plants such as legumes, for example, but not limited to chickpea and field peas (see Table 1). Unexpectedly, it was determined that Amit, CDC ChiChi and CDC Chico chickpeas produce higher levels of D-I as compared to other chickpea varieties (or as compared to many other plants). Also, it was unexpectedly determined that the level of D-I in crude chickpea and field pea extracts could be increased by treating the extracts with light (see Table 5).

The compositions/extracts of the present invention may be employed as nutraceutical or pharmaceutical compositions for the treatment or prevention of one or more diseases, disorders or conditions. For example, as D-I is known to be a potent calcium-activated potassium channel opener (41), it is contemplated that the compositions of the present invention may be used for the treatment of one or more diseases, disorders or conditions that would benefit from a calcium activated potassium channel opener, for example, but not limited to cardiovascular, urological, respiratory, neurological or other diseases, disorders or conditions. Such compositions may be used in vivo or in vitro.

As D-I also has been shown to exhibit insecticidal or antifeedant properties against stored product insect pests (61), the compositions/extracts of the present invention may be employed as insecticidal or antifeedant compositions.

The present invention will be further illustrated in the following examples. For reference, all tables have been inserted at the end of the application.

EXAMPLES

Example 1

Identification of Dehydrosoyasaponin I (D-I) in Chickpea (Cicer arietinum L.)

Seeds and seed processing. Seeds of desi and kabuli chickpea were obtained from the Crop Development Centre (CDC), University of Saskatchewan. The varieties were grown during 2000-2003 in field plots located at the University of Saskatchewan farm, Saskatoon, SK. Amit and Sanford were also grown to maturity in a greenhouse located at Agriculture and Agri-Food Canada, Saskatoon Research Centre. Seeds of Amit, CDC Anna, CDC Xena, Myles and Sanford were ground with a Wiley mill equipped with a 40 mesh screen. Seeds of the other varieties were ground first with a Thomas mill (20 mesh) and finally with a Cyclotec model 1093 sample mill. A Retsch ZM 200 centrifugal mill equipped with a 0.5 mm ring sieve was employed for grinding additional chickpea seed samples of Amit (supplied by the CDC and identified as Goodale 2005 and Goodale 2006), commercially-grown Amit (Walker Seeds Limited, Tisdale, SK), CDC ChiChi (Goodale 2005) and Sanford (Goodale 2005). This centrifugal mill was also used for grinding yellow field pea (CDC Mozart), green field pea (CDC Verdi and CDC Nitouche), lentil (Eston), dry bean (CDC Pintium) and soybean (AC Harmony) samples. Air-classified, protein-rich field pea and desi chickpea flour samples were obtained from Parrheim Foods (Saskatoon). The ground seeds (flours) were defatted with chloroform, extracted with refluxing 80% methanol, filtered and the filtrate was concentrated by rotary evaporation (bath temperature 37-40° C.) until less than 30% methanol remained (4, 21). The concentrated solution was diluted with water (200 mL) and was partially purified by stirring for 24 h with water-washed Diaion™ HP 20 beads (particle size 250-600 µm; porosity 300-600D) from a 180 mL cartridge (Biotage Inc., Charlottesville, Va.). After collecting the beads by filtration, the beads were washed with 30% methanol (500 mL; 30/70 v/v methanol/water). This wash was discarded. The beads were re-washed with 100% methanol (500 mL). The methanol was removed by rotary evaporation and the residue remaining in the flask transferred to a test tube. Evaporation was completed at 43° C. with a centrifugal evaporator (model SC 110A Savant SpeedVac Plus) and the brown powder that remained, designated as an HP-20 MeOH fraction, was dried under vacuum in a desiccator before weighing and HPLC analysis.

HPLC and mass spectrometry. HP-20 MeOH samples (N=3) were prepared in 80% methanol at 8 mg/mL (α-hederin at 0.25 mg/mL) and syringe filtered (0.45 µm pore size, nylon membrane type, Chromatographic Specialties, Brockville, ON) into 0.25 mL glass autosampler vial inserts (Fisher no. 03-375-3A). The solutions were maintained at 15° C. before injection (10 L volume). The instrument consisted of an Alliance 2690 separations module (Waters Canada, Mississauga, ON) equipped with vacuum solvent degassing, a Waters 996 photodiode array detector (PDA) and a PL-EMD-960 evaporative light scattering detector (ELSD) (Polymer Laboratories, Amherst, Mass.) controlled by Waters Millennium software. Settings for the ELSD were attenuation=1, time constant=1 second, temperature=90°, PMT level=6 and airflow=4 liters/min. A reversed phase C-18 Symmetry™ column (3.0×150 mm, 5 µm particle size) purchased from Waters Canada and maintained at 30° C. was used. The mobile phase consisted of 0.05% trifluoroacetic acid (TFA) in water (solvent A) and 0.05% TFA in acetonitrile (solvent B), delivered at a flow rate of 0.4 mL/min. The gradient elution program consisted of 95% A and 5% B at time 0. After 10 min, the composition was 65% A and 35% B (linear, curve 6 gradient). At that time, the linear gradient progressed to 50% A and 50% B over 15 min and to 5% A-95% B over 5 min before reverting to 95% A and 5% B from 35 to 43 min. Mean values of the peak area ratios from single analysis of the three samples from each variety were reported.

Positive ion electrospray ionization mass spectra were obtained with a benchtop tandem quadrupole mass spectrometer (Quattro LC, Micromass UK Limited) equipped with an atmospheric pressure electrospray ionization source interfaced directly to a Waters Alliance 2690 separations module. A reversed phase C-18 Symmetry™ column (2.1×150 mm, 5 µm particle size) held at 30° C. was used. The mobile phase (flow of 0.2 mL/min) consisted of water containing 0.1% formic acid (solvent A) and acetonitrile containing 0.1% formic acid (solvent B). The starting mixture was 95% solvent A-5% solvent B. The gradients were 65% A and 35% B after 10 min, 50% A and 50% B over 15 min and 5% A-95% B over 5 min. Collision induced dissociation (CID) experiments were conducted on the Quattro LC in positive ion mode with argon as the collision gas with collision energies of 30-35 eV. Quasimolecular ions (MH$^+$) were used to generate daughter ion spectra.

Reference samples. Reference samples of biochanin A, biochanin B, ononin and sissotrin as well as the internal standard of α-hederin were purchased from Indofine Chemical Company Inc. (Hillsborough, N.J.). Reference samples of monosaccharides [D(−)-arabinose, D(+)-galactose, D(+)-galacturonic acid, D(+)-glucose, D-glucuronic acid, D-glucuronic acid lactone, D(+)-mannose, R(−)-rhamnose) and D(+)-xylose] were available from Sigma-Aldrich Co. (Oakville, ON). Riboflavin, riboflavin 4',5'-cyclic phosphate, lumiflavin, FMN, FAD and bergapten were also purchased from Sigma-Aldrich. Reference samples of S-I, isolated from soybean and field pea, and reference samples of D-I and S-VI, isolated from field pea, were available from a previous study (61). Additional reference samples of S-I, S-II and S-III were purchased from Chromadex (Santa Ana, Calif.).

Isolation of chickpea saponins. Dehydrosoyasaponin I (D-I) was isolated from a saponin-enriched HP-20 MeOH fraction of Amit chickpea with a reversed phase column of styrene/divinylbenzene operated at alkaline pH (61). Briefly, an AKTAExplorer 100 medium pressure LC (Amersham Biosciences Inc., Baie d'Urfé, PQ) equipped with a 3 mL (6.4×100 mm) reversed phase column packed with 15 µm polystyrene/divinylbenzene beads (Resource 15 RPC, Amersham Biosciences) was used. The mobile phase delivered at a flow rate of 3 mL/min consisted of (A) 0.035% (10 mM) ammonium hydroxide and (B) 0.018% ammonium hydroxide in 50% acetonitrile. The initial conditions were 90% A and 10% B (5% acetonitrile) for 5 min. A linear gradient was applied by increasing the acetonitrile to 24.75% over 13.3 min (13.3 column volumes). Another more shallow gradient to 34.75% acetonitrile was applied during the next 35 min. Thereafter, a 50% acetonitrile concentration was achieved during 7 min and maintained for 5 min before recycling to the initial conditions. Samples for RPC were dissolved in 80% methanol (at a concentration of 10 mg/mL), filtered and about 1 mL (10 mg) was directed with a peristaltic pump (model P-910) to a sample loop (2 mL) and the column. Fractions (0.5 mL) were collected, combined as appropriate and bubbled with nitrogen gas before transferring to test tubes for Savant evaporation at 43° C. Appropriate fractions from four LC runs, utilizing 40 mg of Amit HP-20 MeOH, gave 3.0 mg of D-I (plus 5.7 mg of S-1 and 1.8 mg of impure S-VI). An additional 3.7 mg of D-I was isolated on repeating this experiment (5×10 mg injected). Purification by these techniques of 50 mg (5 runs) of an HP-20 MeOH fraction from the Verano variety gave 4.5 mg of S-I (plus 1.1 mg of impure D-I and 1.8 mg of impure S-VI).

Sugar analyses. Methods for acid hydrolysis (methanolysis) and derivatization (silylation) followed Doco et al. (10) using 0.5 M hydrochloric acid (prepared from acetyl chloride and methanol) and the trimethylsilylating reagent Sylon HTP (consisting of hexamethyldisilazane, trimethylchlorosilane and pyridine, 3:1:9 v/v/v) purchased from Supelco (Bellefonte, Pa.). Reference monosaccharides (0.25 mg) and experimental samples of pea or chickpea soyasaponins (0.3-1.2 mg) were stirred in MeOH/HCl (0.5 mL) for 16 h at 80° C. (Pierce Reacti-Therm III module) and the solvent removed with nitrogen gas (Meyer N-EVAP apparatus). Excess Sylon HTP reagent (0.3 mL) was added and the mixture stirred for 20 min at 80° C. After evaporation to dryness with nitrogen gas, hexane (1 mL) was added with vortex mixing, the samples were concentrated to 200-250 μL and transferred to autosampler vials for electron-impact (70 eV) analysis (5 μL split injections) using a Hewlett Packard 5989A GC/MS equipped with a HP-5 ms column (0.25 μm film thickness, 30 m×0.25 mm i.d.) purchased from Agilent Technologies (Mississauga, ON). The initial oven temperature was 120° C. After 1.0 min, the temperature was raised at 2° C./min to 145° C., at 1° C./min to 180° C. and then at 25° C./min to 280° C. The carrier gas was helium with a 1.5 mL/min constant flow under electronic pressure control.

NMR spectroscopy. Spectra of purified saponin isolates were obtained in pyridine-$d_5$ solution with a Bruker Avance spectrometer operating at 500 MHz ($^1$H).

Results

Figure 2:
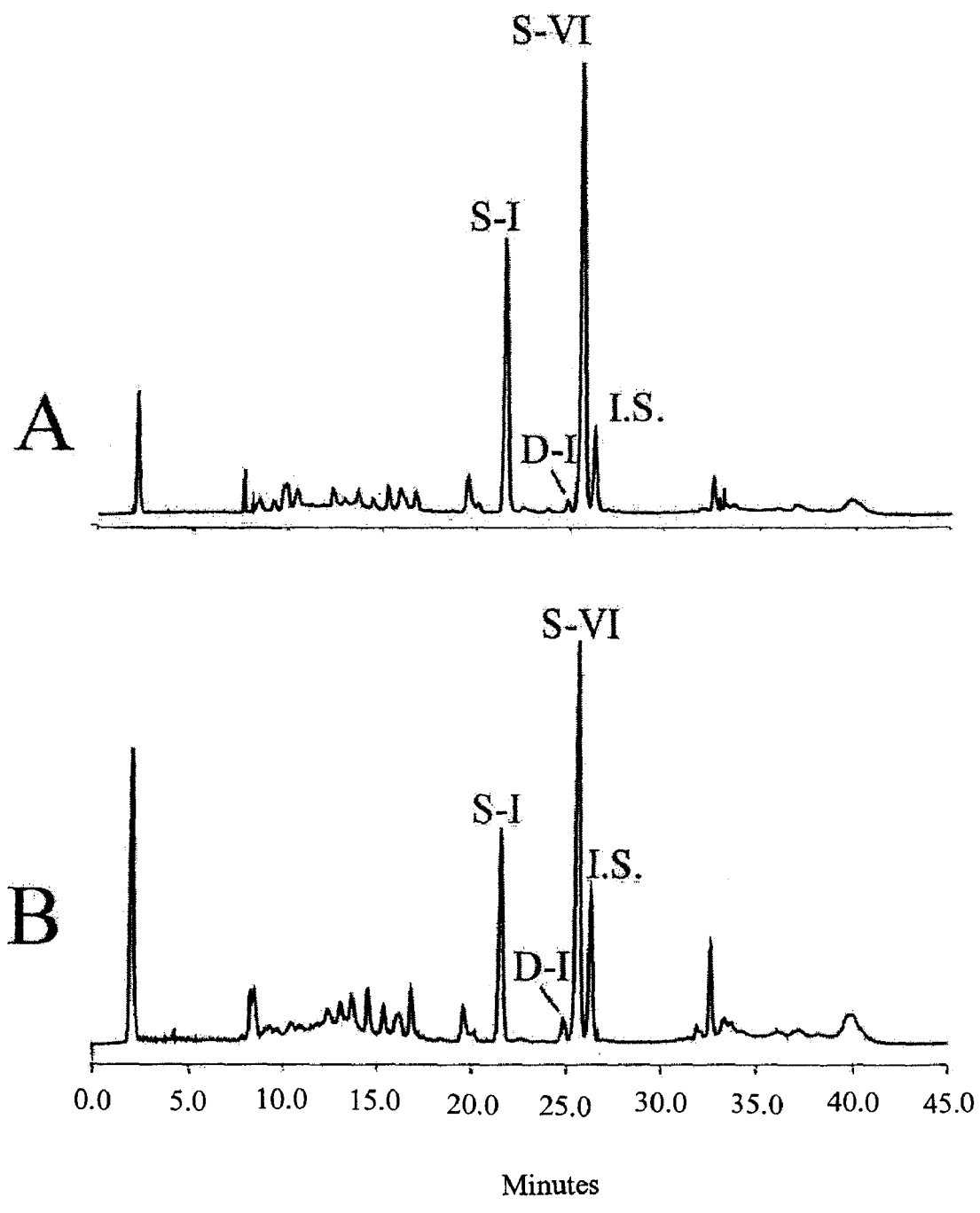
FIG. 2 shows results of HPLC traces with a reversed phase C18 Symmetry™ column and an ELSD detector of HP-20 MeOH fractions from (a) CDC Anna and (b) CDC Xena. The internal standard (I.S.) was α-hederin.

Alcohol and aqueous alcohol mixtures are commonly used solvents for the extraction of saponins from plants. Structures of representative saponins are shown in FIG. 1. In this work, the saponins of defatted chickpea flour were extracted with hot 80% methanol and the crude extracts were cleaned up with Diaion HP-20, a nonionic macroreticular resin also commonly used in saponin isolation chemistry. This isolation was initially performed on flours of CDC Anna and CDC Xena. Examination of the saponin-enriched HP-20 MeOH fractions by C-18 HPLC and with α-hederin as internal standard showed S-VI as the major saponin (FIG. 2), in agreement with published HPLC traces of n-butanol extracts from other chickpea varieties (53). HP-20 MeOH fractions of CDC Anna and CDC Xena also contained detectable concentrations of S-I and D-I. The identity of S-I, D-I and S-VI was established by HPLC/MS comparison to reference samples of these compounds isolated from soybean and field pea extracts (61).

On assessing by HPLC peak area ratios the distribution of soyasaponins in HP-20 MeOH fractions, the total soyasaponin concentration was higher for CDC Anna but the concentration of D-I appeared to be lower compared to CDC Xena, a kabuli variety. We therefore extended this study to include other desi and kabuli varieties of commercial chickpea seeds, with the primary objective of analyzing the seeds for elevated levels of D-I.

In the desi chickpea varieties (Table 1), D-I was detected in extracts from all of the seeds but the concentrations were low and about the same as in the extract from CDC Anna. CDC Cabri and CDC Desiray showed the highest levels of total soyasaponins (S-I+D-I+S-VI), with S-VI predominating. Myles was next.

In several of the kabuli chickpea varieties (Table 1), we discovered that HP-20 MeOH fractions from field-grown seeds contained concentrations of D-I that were 5-15 times higher than those of CDC Xena. The Amit variety gave the highest peak area ratio of D-I to internal standard, followed by CDC ChiChi, Sanford, CDC Chico, CDC Yuma, and Dwelley. In these varieties, saponin fractions of CDC Yuma followed by Amit showed the highest total soyasaponin concentrations. It was noted that a single kabuli variety (CDC Frontier) had high levels of S-VI (equivalent to CDC Yuma, CDC Cabri and CDC Desiray) but low levels of S-I and D-I. CDC Diva, like CDC Xena, had low concentrations of all three soyasaponins. The concentration of S-I varied from a high with Amit and CDC Verano, to a low with CDC Diva.

It was noted that the HP-20 MeOH fraction of CDC Verano, a variety with green colored seed, showed predominantly S-I, suggesting that S-I occurred naturally in seeds of CDC Verano. However, it must be recognized that levels of S-I can be dependent on a number of conditions that influence the extent of conversion of S-VI to S—, including the temperature and duration of solvent evaporation and the time an extract remains in alcoholic solution prior to HPLC analysis (22, 29, 61). The extract from a commercially-milled sample of desi chickpea also showed an elevated level of S-I. Further, as showed herein, S-I may be produced preferentially over other soyasaponins under specific conditions of treatment with light. Accordingly, the present invention also contemplates methods of producing soyasaponin S-I (S-I) by subjecting compositions comprising soyasaponin S-VI (S-VI) to light as shown herein.

For comparison, an HP-20 MeOH fraction from commercial field pea flour was isolated in the laboratory and analyzed by HPLC. The results shown in Table 1 suggested that field peas were a source of D-I, like CDC Diva, CDC Xena, CDC Frontier and the five desi varieties, although the levels of D-I were not as high as other chickpea varieties. Total soyasaponins in the pea fraction were at about the same concentration as in CDC Xena and slightly higher than in CDC Diva and Dwelley.

Figure 3:
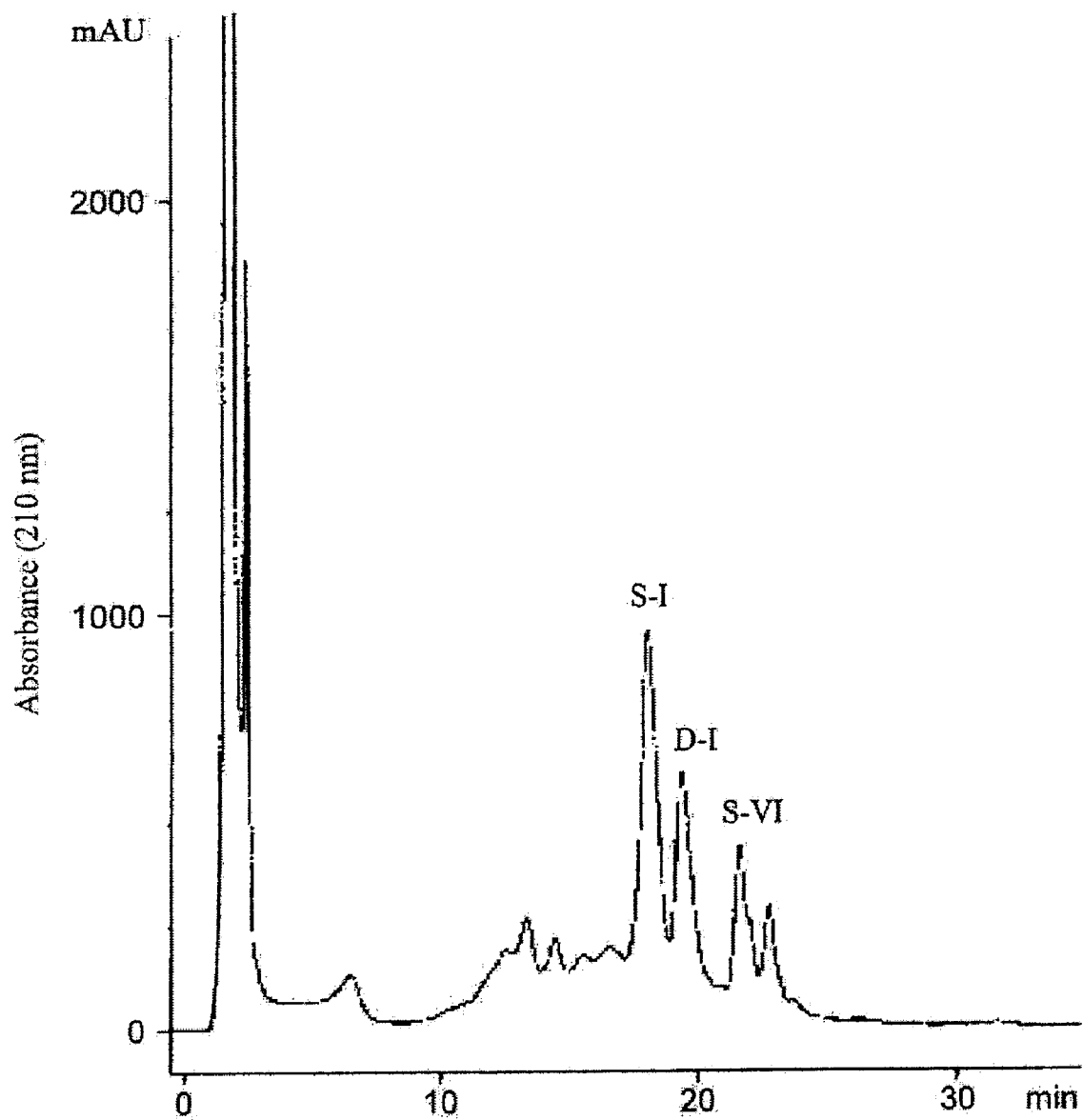
FIG. 3 shows a chromatogram illustrating the LC separation (210 nm detection) by medium pressure reversed phase chromatography (Resource 15 RPC column) of S-I, D-I and S-VI contained in an HP-20 MeOH fraction of Amit chickpea (10 mg injected).

Although the absolute levels of D-I were not determined by HPLC, it was relevant to demonstrate that this rare but potentially valuable soyasaponin could be isolated from a chickpea variety. The HP-20 MeOH fraction from field-grown Amit was chosen for this work. With a reversed phase column of styrene/divinylbenzene operated at alkaline pH (61), the soyasaponins were adequately resolved and collected with a medium pressure LC designed for microgram to milligram scale isolations (FIG. 3). The identity of isolated samples of S-I, D-I and S-VI was confirmed by electrospray HPLC/MS. In 80% methanol, the isolated samples appeared to be of high purity except that S-VI had been partially hydrolyzed to S-I. The isolated yield of D-I was 7.4-7.5% (from the HP-20 MeOH material). Using the techniques described here, about 25 mg of D-I could be isolated in theory from 100 grams of defatted Amit flour. The overall yield (0.024%) appeared to be at least four fold higher than yields from other botanical sources of D-I (Table 2).

During electrospray HPLC/MS on the MeOH fractions from Amit and Sanford, the peak corresponding to D-I was selected for CID experiments. Daughter ions derived from the quasimolecular ion at m/z 941 were found that corresponded to the loss of one (terminal rhamnose), two (rhamnose, galactose) and three sugar units (rhamnose, galactose, glucuronic acid). These ions, at m/z 795, 633 and 457, as well as ions from additional loss of the elements of water, have been observed before in CID experiments on D-I isolated from field pea (61). The trisaccharide sequence therefore appeared to be the same in isolates of pea and chickpea. However, additional evidence was sought, particularly on the possibility that other hexoses besides galactose were present in samples of D-I (and S-I) from the chickpea. In this regard, legume saponins with rhamnose, glucose and glucuronic acid at C-3 have been described, for example dehydroazukisaponin V (molecular weight of 940) and azukisaponin V (942) from *Trifolium alexandrinum* (44). Isobaric glucose-containing saponins would not likely be differentiated from those containing galactose (or mannose) by CID techniques.

We therefore sought a technique to liberate monosaccharides from the experimental saponin samples and to identify the resulting sugars. Of the available methods applicable for neutral sugars and uronic acids (3), we chose a GC/MS method (with a HP-5 capillary column) based on methanolysis of polysaccharides with methanol containing hydrochloric acid and conversion of resulting methyl ethers to their trimethylsilyl (TMS) derivatives. As illustrated by Doco et al. (10) with pectic polysaccharides and a DB-1 capillary column, the derivatized monosaccharides gave several components for each sugar, corresponding to the α- and β-anomers, and pyranose and furanose ring forms. Ions obtained from GC/MS on each component helped to characterize the usual sugars as pentoses, hexoses, 6-deoxyhexoses or uronic acids.

Figure 4:
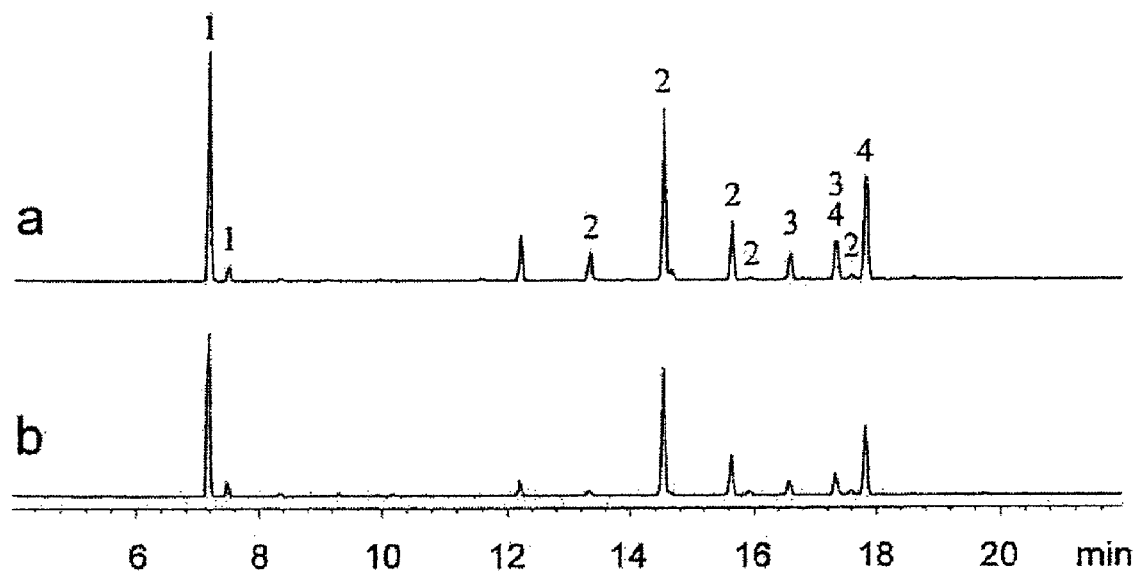
FIG. 4 shows total ion mass chromatograms from GC/MS analysis (HP-5 column) of the TMS methyl ether derivatives of sugars obtained after methanolic-HCl treatment of Amit chickpea isolates of (a) D-I and (b) S-I. The detected monosaccharide derivatives are labeled as 1 (rhamnose), 2 (galactose), 3 (glucose) and 4 (glucuronic acid). The unlabeled peak at 12.2 min appeared to be an artifact arising from the derivatization of sugar components.

Following methanolysis and TMS derivatization of a purified sample of D-I from Amit, the total ion chromatogram from GC/MS (FIG. 4) showed as expected that the principal monosaccharides were rhamnose (2 main peaks), galactose (5 peaks) and glucuronic acid (2 peaks), assigned by comparison to the GC/MS data obtained from reference samples of these sugars. However, another component produced from D-I was present, eluting at 16.6 min. This component was assigned to glucose because derivatized glucose gave a main peak at this retention time with the same mass spectrum (in addition to a smaller peak at 17.3 min that interfered with a peak from glucuronic acid). The small unassigned peak at 12.2 min did not arise from D-I because this component was found in HP-5 chromatograms of reference mixtures of rhamnose, galactose and glucuronic acid and of reference mixtures of rhamose, galactose, glucuronic acid and glucose. It was not observed during GC/MS following methanolysis and derivatization of solvent or single sugar components. The lower trace of FIG. 4 shows the monosaccharides identified in a sample of S-I isolated from Amit. The sugar profile was the same as for D-I, again indicating glucose was present as a contaminating sugar, probably replacing galactose, the middle sugar, at C-3. GC/MS analysis of derivatized samples of S-I available from soybean and field pea extracts (61) suggested that S-I isolates from soybean, like chickpea, were contaminated with a glucose-containing glycoside whereas field pea sources were not. Glucose was also detected in an impure sample of S-VI from chickpea.

Figure 5:
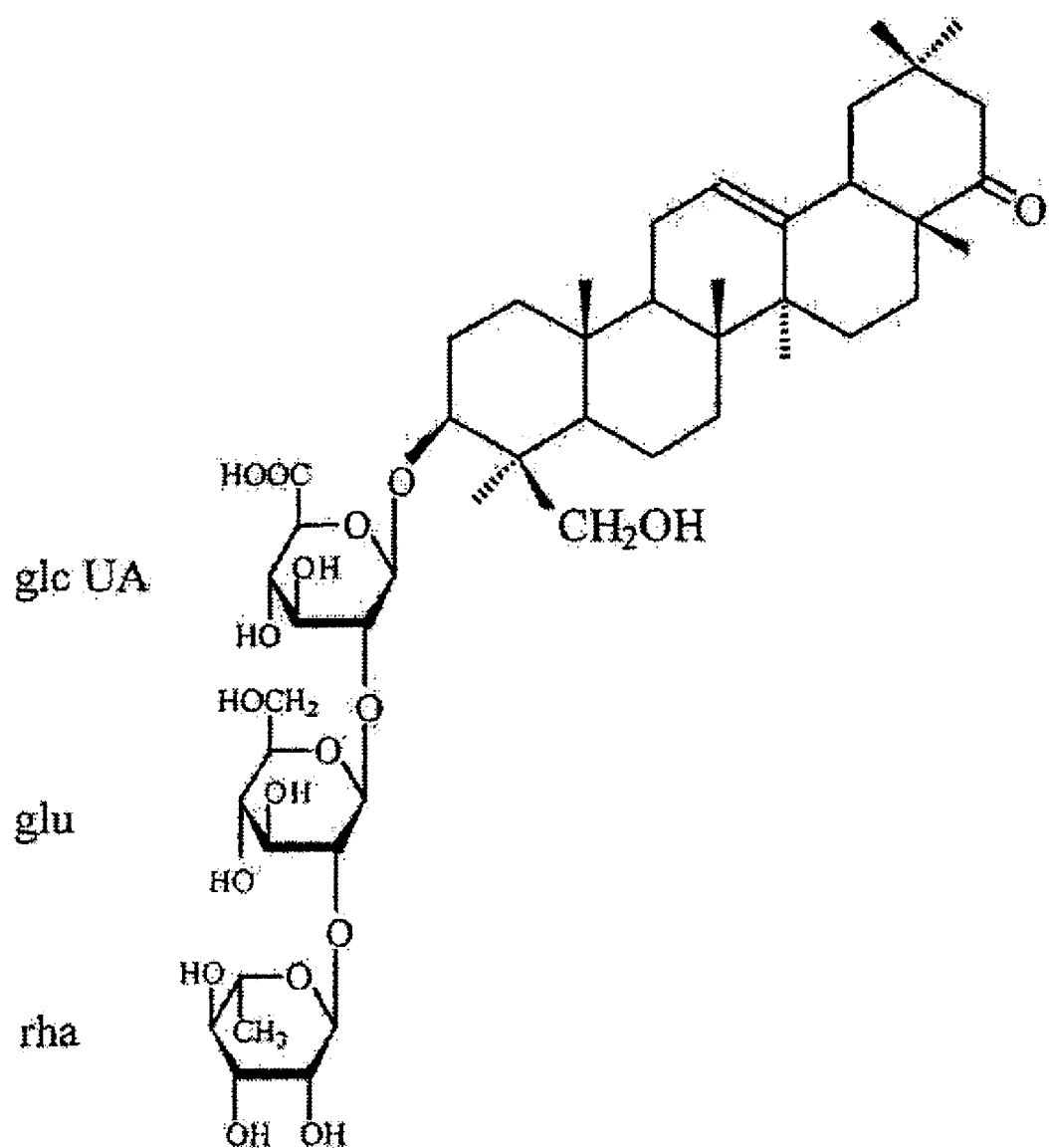
FIG. 5 shows the structure of dehydroazukisaponin V, a proposed minor saponin component of chickpea.

It was of interest to examine some of the isolates by NMR spectroscopy to determine if a minor glucose-containing glycoside could be detected. In agreement with reported proton NMR data (44, 56), we found that the sample of D-I from Amit gave a broad singlet for rhamnose H-1 at 6.31 ppm and a prominent doublet (J=7.5 Hz) for galactose H-1 at 5.82 ppm. This sample also gave weaker signals at 6.43 ppm (singlet) and 5.90 ppm (doublet), integrating respectively for 17-23% of the main singlet (at 6.31 ppm) and the main doublet (at 5.82 ppm) for D-1. Chemical shifts of these minor signals were in agreement with those of rhamnose H-1 and glucose H-1 reported for the methyl ester of dehydroazukisaponin V (FIG. 5) in pyridine solution (44). Samples of S-I isolated from Amit and CDC Verano also gave detectable signals at 6.43 ppm and 5.90 ppm, in accord with the minor glucose-containing glycoside being azukisaponin V (31, 44). As expected from the GC/MS results, the NMR signals attributed to glucose instead of galactose in the trisaccharide unit were undetectable in an isolate of S-I from field pea.

The results provided herein suggest that chickpeas, and in particular, kabuli varieties identified here are potentially good sources of D-I for medicinal, herbal and insecticidal applications, recognizing that soyasaponin fractions isolated from the chickpea may also contain about 20% of azukisaponins or closely related triterpenoids (37, 57, 58) as contaminants.

Example 2

Effect of Ordinary Fluorescent Light on the Production of D-I

Laboratory experiments were conducted to determine chickpea soyasaponins (S-I, D-I and S-VI) by HPLC with an evaporative light scattering detector (ELSD) by adopting the method of Ganzerra (16) for soybean saponins. Their method, utilizing 1 gram of soybean flour and 80% methanol as solvent, was applied to flour of CDC Chico (1 g, not defatted), a kabuli chickpea variety with moderate levels of D-I contained in Diaion HP-20 methanol extracts from 100-gram scale extractions with 80% methanol.

After extraction at room temperature of the Chico flour and centrifugation, the 80% methanol extract was diluted to 10 ml and a 0.3 ml aliquot was transferred to a vial for HPLC/ELSD analysis. Similar tests were conducted by performing the extractions not only at room temperature but also under reflux (for 5, 15, 30 and 60 minutes), using 4 ml of 80% methanol and with and without treatment of the crude extracts with various types of Diaion HP-20 beads.

HPLC observations from a further experiment (Table 3) showed the levels of D-I dramatically increased (at least a 10-fold enhancement) by storing the crude chickpea extracts in the laboratory for 7 days. Brief storage in the laboratory or storage in the refrigerator for 7 days had little effect on levels of D-1. Without wishing to be bound by theory or limiting in any manner, the chickpea extracts may comprise an unknown factor or catalyst that was capable of producing D-I or aiding in the production of D-I.

Further insight was provided by an additional experiment (Table 4). Since previous reports that D-I levels were elevated in extracts obtained with 80% methanol containing EDTA, a metal-ion chelating agent added directly to solvents for extraction of labile natural products including those from soybean (71), without wishing to be bound by theory, it was unlikely that D-I was produced by a co-extracted metal-ion oxidant such as the ferric ion. On the other hand, ferric chloride has been reported (48, 49) to oxidize S-VI to S-I (3 parts) and D-I (2 parts). Levels of S-I in the chickpea extracts remained relatively constant, an observation that also did not support the oxidation theory by ferric ions.

Utilization of amber glass vials and foil-protected glass vials greatly inhibited the production of D-I. Without wishing to be bound by theory or limiting in any manner, this suggests that D-I was produced by the action of light. Further, since the levels of S-VI were dramatically reduced by storage of crude extracts in clear glass vials and remained elevated in amber glass or foil-protected glass, it is possible that D-I was a photoproduct of S-VI. S-VI from other plant sources was known to be labile under basic or acidic conditions and on standing in aqueous alcohol solutions, producing S-I and maltol, as recently discussed (19). Without wishing to be bound by theory or limiting in any manner, it was noted in this work that S-VI in alcohol-based solvents, for example, but not limited to 80% methanol was labile to fluorescent light levels typically encountered in a laboratory, and capable of producing D-I in quantity after a few days of exposure at room temperature.

Previous work in our laboratory with pea and lentil extracts, both of which had levels of S-VI comparable to those of the chickpea, did not show high concentrations of D-I by HPLC. Without wishing to be bound by theory or limiting in any manner, this suggests that the chickpea flour may contain an additional factor co-extracted with S-VI and capable in the presence of light of converting or assisting in the conversion of S-VI to D-I. If the concentration of the factor was variety dependent, then one would expect varying levels of D-I in chickpea extracts. S-VI of an unspecified legume source was reported in a book chapter to decompose to D-I (in up to 30% yield) when samples containing S-VI were kept in chloroform solution for prolonged periods of time (39). Although a mechanism was proposed for decomposition in solution to S-I and to D-I (with arrows depicting electron shifts to attempt to explain the formation of these artifacts), the authors did not mention or suggest the possibility of light-promoted degradation or photoconversion of S-VI.

It was of interest to determine if variety effects were evident, as shown previously in Table 1. The same desi and kabuli flours were studied by extracting and then storing the extracts briefly and for 7 days under ordinary laboratory conditions of temperature and light. In the 7 day treatments, the crude extracts were stored in clear glass vials on the countertop of a laboratory with approximately a 12 hour day-light cycle with regular fluorescent lights. Each sample, located about 1.5 meters from the nearest fluorescent tube, was processed with Diaion HP-20 beads before HPLC/ELSD analysis (Table 5).

In comparison to brief laboratory storage, levels of D-I were elevated on extended storage of crude extracts from both desi and kabuli types. It was also true that Amit, including a commercial field sample of Amit, showed by far the highest levels of D-I. These observations were in agreement with previous conclusions, where the 100-gram scale crude extracts were stored in the laboratory for up to 4 days prior to Diaion HP-20 treatment. It was concluded that variety effects could easily be detected in extracts obtained at room temperature followed to exposure to ordinary laboratory conditions for 7 days. One of the kabuli varieties (Amit) was confirmed as a preferred source of D-I. However, other varieties high in soyasaponin S-VI (S-VI) are also contemplated.

Example 3

Isolation and Detection of D-I in Methanol Extracts from Other Plant Species

Using the one gram scale procedure as described previously in the examples, we extracted the flour of field pea (a sample from a commercial mill) and lentil (seeds were of the Laird variety) with 80% methanol, with the exposure of the crude extracts briefly and for 7 days to laboratory light. These species, like chickpea, were known to have soyasaponin VI (S-VI) as a prominent saponin. Both species showed an increase in D-I with prolonged exposure to light (Table 5).

Additional flour samples of yellow field pea, green field pea, lentil, soybean and dry bean were studied, using the traditional 100 gram scale method of flour extraction and with exposure of the crude 80% methanol extracts to light (as described for the samples of Table 1) and to more intense light from a growth cabinet. For comparison, a flour sample from commercially-grown Amit chickpeas was processed under these same conditions. Diaion HP-20 methanol extracts were isolated and examined by HPLC (Table 6). The level of D-I found in the Amit extract was higher following cabinet light treatment compared to the level of D-I found in extracts of the same flour treated with laboratory light of lower intensity (see also Table 5).

Under conditions of brief exposure to laboratory light, extracts obtained from yellow and green field peas showed intermediate levels of S-VI and low levels of D-I. Cabinet light treatment promoted the formation of D-I in the extracts from yellow peas. Green pea extracts of CDC Verdi and CDC Nitouche gave D-I levels that were only slightly elevated following light treatment and about 20 times lower than those from yellow pea extracts. However, levels of S-I were twice as high compared to yellow peas. The light-treated yellow pea extracts were considerably lower in D-I compared to the Amit chickpea extract. The D-I index for yellow peas was 6-7 compared to about 140 for Amit. Without wishing to be bound by theory or limiting in any manner, extracts from green peas (D-I index of 0.3-0.4) may be lacking an unknown factor that promotes the degradation by light of S-VI to D-I. However, S-VI of green peas was efficiently converted to S-I, probably by a non-light activated process. The Eston lentil variety, with moderate levels of S-VI detected in extracts prior to light treatment, behaved similarly to green peas with light treatment. Conversion to D-I was low. It was previously shown that aqueous methanol extracts from peas and lentils contain insecticidal PA1b peptides (62. 63). The PA1b peptides were also detected in the present extracts from these species.

Regarding the dry bean sample of CDC Pintium, it was initially thought that D-I was present in quantity in the extract isolated without light treatment. However, LC/MS analyses showed that an interfering component (1084 Da) with the same retention time as D-I was present. D-I was only detected after light treatment, co-eluting of course with the interfering peak. The potential for D-I production in extracts from CDC Pintium was compromised because of relatively low levels of S-VI. This was reflected in the low D-I index after light treatment, estimated at 2.3.

Figure 6:
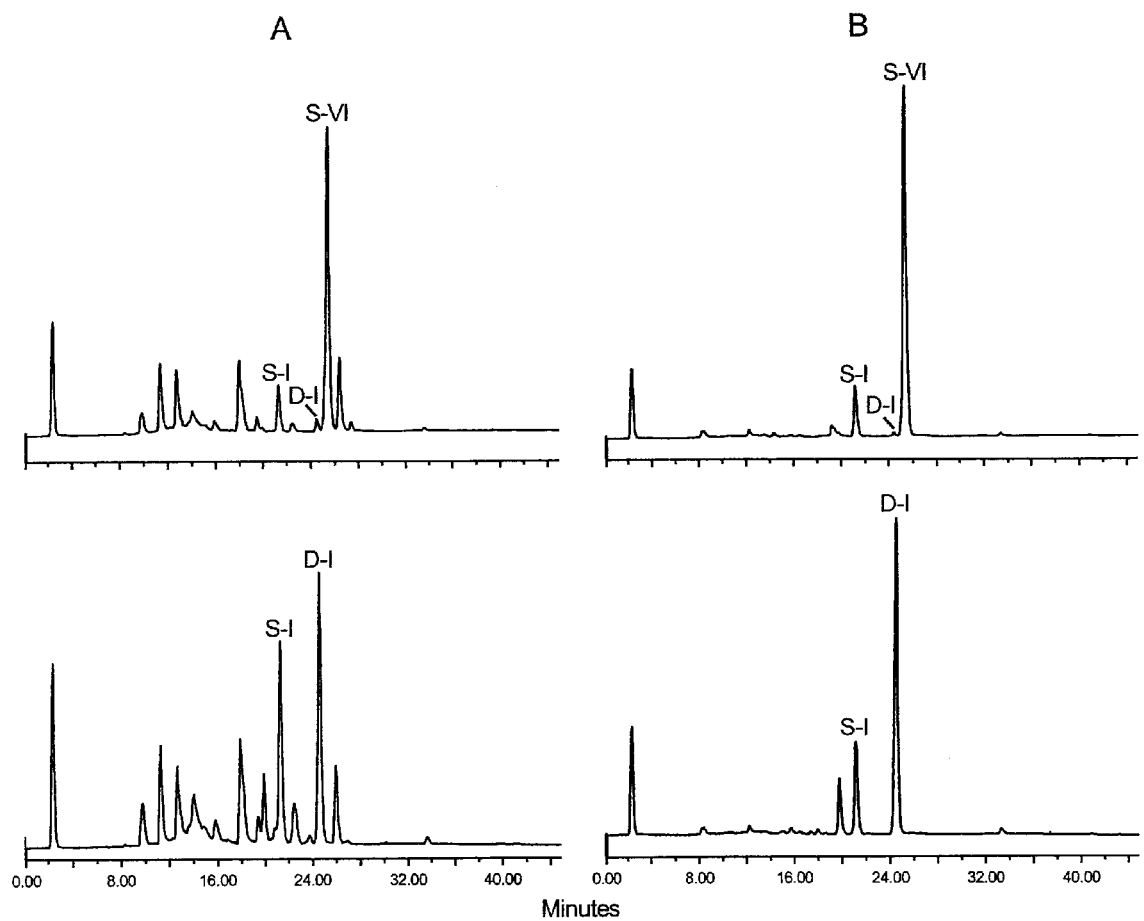
FIG. 6 shows HPLC/ELSD chromatograms from a C18 Symmetry column of HP-20 MeOH fractions from (a) soybean (variety AC Harmony) and (b) chickpea (Amit or B-90) isolated before (upper) and after (lower traces) fluorescent light treatment of the crude 80% methanol extracts from the defatted flours. The lower traces did not show S-VI in detectable concentrations. Internal standard was absent from these samples.

The defatted soybean sample of AC Harmony showed many components during HPLC, including a component with the same retention time as the internal standard. Hence, the peak area ratios were estimated by reference to peak areas of other chromatograms containing the internal standard. HPLC/ELSD traces of the soybean extracts with and without light treatment were compared to those of Amit, also minus the internal standard (FIG. 6). In the region of elution of soyasaponins B and E (soyasaponins of the A type present in soybean are more polar and consequently have shorter retention times), it was found that S-VI levels were higher than those of peas, beans or lentils but considerably less than those of the extract from Amit. Like Amit, D-I could also be detected in the non-light treated extract from soybeans, in agreement with the literature (32). It was also true that light treatment enhanced D-I levels about 10-fold (the Amit extract showed a 100-fold enhancement). The D-I and purity indices, 32 and 95 respectively were considerably less than the same indexes of the sample of Amit (about 143 and 551, respectively). Nevertheless, soybeans showed promise as a source of extracts partially enriched in D-I. It was also interesting that the area of the peak eluting before S-I (at 19.8 min in FIG. 6) had increased following exposure to light of both the soybean and chickpea extracts. This common photoproduct gave a molecular mass of 1029 Da by LC/MS (MH+ 1030). Yields of the saponin-enriched extracts from soybean were higher than from any of the other crops.

Example 4

Solvent Extraction Experiments

The ability of different solvents to extract soyasaponins was tested. We compared methanol and ethanol mixed in various proportions with water (100-0, 95-5, 75-25, 50-50, 25-75, 5-95 and 0-100 (v/v)) by first extracting Amit chickpea flour (1 g) at room temperature with each of the specified solvents and then exposing to fluorescent light 0.5 ml aliquots of the crude extracts for periods of 0, 1, 2, 4, and 7 days at 21 degrees C. The samples in clear glass vials were exposed to light in a Controlled Environment Chamber (Hoffman Manufacturing, Inc., model SG2-22) equipped with 6×40 Watt fluorescent lights (4 ft), Cool White type, 3 mounted vertically on the back and 3 on the front (door). Samples were placed on the center rack of the chamber (internal width 50 cm×depth 68 cm×height 150 cm). The production of D-I was followed in the crude extracts by thin layer chromatography. D-I appeared as a purple spot after development with chloroform:methanol:water (60:40:10 by volume) and spraying the plate with freshly prepared Liebermann-Burchard reagent. Based on the experiments conducted, some of the conclusions from viewing the TLC plates were (a) D-I was extracted in aqueous ethanol as well as aqueous methanol; (b) D-I was not found in pure methanol, ethanol or water, and (c) the tests suggested that D-I was efficiently extracted and produced in 75% methanol (comprising 25% water) or in 50% ethanol (comprising 50% water), with exposure to chamber lights for 1-2 days. Similar results were obtained for other alcohol/water solvents (data not shown).

Example 5

Processing and Light Cabinet Experiments with Methanol and Ethanol

With information derived from the 1-gram scale aqueous alcohol experiments of example 4, it was relevant to experiment on the larger 100-gram scale, with the aim of economically improving the processes leading to isolation of D-I enriched extracts and to purified samples of D-I. It was worthwhile to compare methanol to ethanol for isolation of saponin fractions by Diaion HP-20 bead technology. To that end, extraction solvent systems of 80% methanol and 60% ethanol were compared, starting with raw flour (flour that had not been defatted) from commercial Amit chickpeas. These solvent mixtures were similar to the compositions employed in example 4 but with 5-10% higher alcohol content (the slightly higher alcohol content greatly enhanced the speed of filtration of the crude extract following extraction). For economic reasons, a relatively low solvent to flour ratio of 5 to 1 was employed, with the extractions conducted by stirring for 4 hours at room temperature (ca. 21° C.). Fluorescent light exposure periods in a Controlled Environment Chamber at 21° C. were set at 2 days (for methanol) or 3 days (for ethanol). Prior to addition of HP-20 beads, reduction in alcohol concentrations by the conventional rotary evaporation method was compared to the faster, more energy friendly method of dilution with water (polymeric adsorbents are most frequently used with pure water but Diaion HP-20 beads can tolerate methanol concentrations up to about 30%). Although methanol was recognized as a preferred solvent for washing the beads to obtain extracts of natural products, the literature contained examples of the use of Diaion HP-20 with ethanol (25, 28). A further objective was to demonstrate (with a custom-prepared reverse phase column for a medium pressure LC) if samples of purified D-I could be obtained from these saponin-enriched extracts.

HPLC examination of the isolates from these experiments showed that D-I enriched extracts could indeed be isolated from raw Amit chickpea flour by either methanol or ethanol solvent systems (Table 7). Methanol tended to produce extracts with lower concentrations of S-I as seen in the slightly lower S-I to internal standard ratios for this solvent. Peak area ratios of D-I to internal standard were higher with methanol (7.0-8.1) than with ethanol (6.8-7.1). With the dilution technique, small increases in total saponin levels were seen with both solvents compared to extracts obtained by solvent evaporation. This accounted for the lower D-I to total saponin ratios for ethanol (0.5) compared to these ratios for methanol (0.6-0.7). An unretained HPLC peak (probably a complex mixture of very polar organic or inorganic substances) represented the majority of alcohol-soluble material isolated by washing the HP-20 beads with aqueous methanol or ethanol (but see example 7 for LC/MS identification of retained chickpea components detected in these fractions).

Saponin-enriched fractions from trials 1 and 3 were selected to demonstrate the feasibility of isolating purified samples of D-I after light treatment in methanol and ethanol, using a reversed phase column of styrene/divinylbenzene at alkaline pH as described in example 1. By employing a larger column (24 ml) and sample load (50 mg per injection), it was possible to isolate highly purified samples of D-I from these crude extracts. The isolated yield of D-I was 0.019% from both experiments. This yield, although less than the 0.024% yield obtained with the previous Diaion HP-20 MeOH extracts isolated (according to Table 1) from defatted Amit chickpea flour, was reasonable considering that the starting flour had not been defatted, the solvent to flour ratio was relatively low and the column was larger. The D-I isolates were of high purity by HPLC. NMR analyses again showed the presence of dehydroazukisaponin V as a minor component.

Three different samples of Amit chickpea flour (described under footnotes f, g and h of Table 5) were selected for further studies with 60% ethanol at room temperature, with brief and 3 day cabinet exposure to fluorescent lights, with dilution to reduce the ethanol concentration and with isolation of Diaion HP-20 ethanol fraction only (Table 8). On examination by HPLC/ELSD, these samples did not reveal a lot of difference under conditions of brief exposure to light, similar to the 1-gram scale experiments with brief light exposure in 80% methanol (Table 5). Following 3 days of cabinet light, Walker 2005 and Goodale 2005 gave similar S-I to internal standard ratios (7.5-8.3). The higher S-I ratio for Goodale 2006 (12.5) contributed in part to the lowest value of 0.3 for the D-I to total soyasaponin ratio, a trend also seen previously with this flour sample exposed for 7 days in 80% methanol (Table 5). Without wishing to be bound by theory or limiting in any manner, it seemed that the pathway of S-VI to S-I was preferred over the pathway to D-I in Goodale 2006. The D-I to internal standard ratio was 8.5 with Amit 2005, compared to values of 4.7-6.2 for the other samples. Hence, in the experiments conducted, Walker 2005 showed the highest D-I to total soyasaponin ratio (about 0.5) and D-I index (about 138). Purity indexes were 352 (Walker 2005), 167 (Goodale 2006) and 145 (Goodale 2005). One could conclude that some variability would be expected in the final concentrations of D-I (and S-I) when light-treated ethanol extracts are isolated from different sources of Amit chickpeas, including probable interactions of variety with site and year of growth (environment). Effects of genetics and environment on levels of phytochemicals have been well documented, including soyasaponins of Australian sweet lupin (54).

It was of interest to study other sources of light, which would have practical implications especially in pilot-scale extractions, and which might help to characterize the additional factor capable of producing, or aiding in the production of, D-I in crude legume extracts. Experiments were therefore performed with Amit chickpea flour, using 80% methanol and 60% ethanol as extraction solvent and with three types of lights available for a small laboratory photoreactor. The sources included Cool White fluorescent lights (for comparison to fluorescent lighting of the larger Controlled Environment Chamber), UVA fluorescent lights (centered near 350 nm) and fluorescent lights of the UVC type (254 nm). Trials were also performed with sunlight (Table 9). Sunlight reaching the earth surface is composed of about 91% visible (400-700 nm), 8.7% UVA (320-400 nm) and 0.3% UVB (290-320 nr) (69). UVC (200-290 nm) does not reach the earth surface.

After 2 days of exposure of the crude extracts in aqueous methanol solution, the four light sources reduced the level of S-VI to below the detection limit. HPLC/ELSD also showed that the production of D-I was elevated considerably (D-I to internal standard ratios of 7.8-8.7), except for UVA (about 4.2). Regular fluorescent light, UVC and sunlight produced nearly equal concentrations of D-I and S-I whereas UVA in methanol gave S-I predominantly. Sunlight was a suitable light source for the production of D-I in methanol.

In ethanol, nearly all of the S-VI had also disappeared after exposure regardless of the light source. However, more S-I than D-I was produced, except during exposure to UVC. This result was apparent in the relatively low D-I to total soyasaponin ratio of 0.2. The ratio was 0.5 for UVC.

Compared to HPLC results from the larger cabinet (see the Walker 2005 entry of Table 8), the higher light intensities encountered from Cool White fluorescent tubes of the smaller cabinet may have contributed to higher than anticipated levels of S-I with ethanol as solvent. In methanol, the same trends were apparent. S-I concentrations were also higher with ethanol and mid summer sunlight than with methanol and sunlight exposure in early fall. It appeared that visible cabinet light of about 2,000-2,500 lux was preferred for production of D-I.

In addition to the known propensity of S-VI to decompose in solution to S-I (and maltol), without wishing to be bound by theory or limiting in any manner, the present results suggest that this conversion to S-I was enhanced by visible light intensity of greater than about 8,000-10,000 lux and by UVA.

Good conversion of S-VI to D-I was promoted by light in the visible range and with methanol as solvent. But the longest wavelength of absorption reported for S-VI occurred at 295 nm (65). Without wishing to be bound by theory or limiting in any manner, this suggests that another compound present in crude chickpea extracts was capable of absorbing visible light, leading to mediation of sensitized photodegradation or phototransformation of S-VI (and that in the absence of the additional compound, S-VI would be stable to visible light). Compounds that act as described (through photoabsorption of daylight) are known as photosensitizers. Under aerobic conditions, they are capable of generating reactive oxygen species and free radicals after excitation with appropriate light and are classified as Type I (free radical) or type II (singlet oxygen), depending on reaction mechanisms involved. Riboflavin (vitamin B2), a prominent example of a photosensitizer acting under visible light conditions (up to about 500 nm), can act by both mechanisms (7). The literature on riboflavin as a visible light sensitizer in the photodegradation of various drugs has recently been reviewed (17). Many substrates such as herbicides, fungicides, antibiotics and bilirubin can be photodegraded in solution in the presence of riboflavin at an extremely low concentration. Other photosensitizers include Rose Bengal, Methylene Blue, benzophenone, menadione, titanium dioxide, humic acid, hydrogen peroxide and various porphyrins (tetrapyrroles). Six natural photosensitizers were detected in butter, including riboflavin, protoporphyrin, hematoporphyrin, a chlorophyll a-like molecule and two unidentified tetrapyrroles (68). Naturally-occurring furocoumarins (psoralens), widely distributed in plants of Rutaceae, Moraceae, Apiaceae and Leguminosae and used for many years in photochemotherapy, are often classified as photosensitizers, although they absorb UVA light (5). Furans and related molecules can also act as singlet oxygen scavengers, like vitamin C.

UVC also generated D-I in quantity, again suggesting that D-I was a photoproduct of S-VI.

Example 6

Mixing Experiments Designed to Search for a Photosensitizer

To further investigate the possibility of S-VI undergoing visible-light-mediated phototransformation to D-I, a source of the unstable S-VI was required as well as other chromatographic fractions that might contain a photosensitizer. Starting with defatted Amit chickpea flour and with brief (minimal) exposure to visible laboratory light, we therefore isolated by the traditional hot methanol and Diaion HP-20 procedures (of Table 1) a dried HP-20 MeOH extract containing S-VI. The earlier-eluting aqueous methanol fractions (also isolated in powder form) were additionally obtained as a potential source of the photosensitizer, in addition to the chloroform extract from the defatting step. Three extraction and isolation experiments were completed (prep A, B and E). Aqueous methanol fractions (30% MeOH and <30% MeOH) containing non-saponin components (see example 7) were additionally available from an experiment on the same flour but these fractions had been isolated after exposure of the crude methanol extract to light (see Table 7).

In trial 1, none of the additions triggered a dramatic change in D-I or S-I concentrations (Table 10). However, the concentrations of S-VI tended to decrease, except at high addition of the chloroform fraction. The D-I to total soyasaponin ratio did not exceed 0.1 following any of the additions. This ratio was 0.09 in the two control extracts without additions. Since the fractions isolated for addition were obtained after light treatment, any potential photosensitizers may have been unstable in light and the expected effects of increased levels of D-I would have been nullified. The present results could be explained if riboflavin was the photosensitizer because riboflavin in aqueous solution has been shown to be unstable to visible light (2, 23). Further, we found that riboflavin was soluble in 80% methanol (but sparingly soluble in chloroform).

In trial 2, the first experiment was repeated but with the fractions for addition isolated under minimal light conditions (Table 10). The extract enriched in S-VI gave a D-I to internal standard ratio of 0.5 before light treatment whereas this ratio increased to 1.9-2.1 after light treatment. Addition of the <30% MeOH fraction or the 30% MeOH fraction raised the D-I to internal standard ratios even higher (3.4-4.4) whereas addition of the chloroform extract had little effect on D-I levels. Without wishing to be limiting or bound by theory, this suggested that a photosensitizer was present in the aqueous methanol fractions. A photosensitizer also seemed to be present in the main saponin fraction but in concentrations that were only partially effective. The chloroform fraction did not appear to contain a photosensitizer in significant concentrations.

A third experiment was conducted in the same manner as trial 2 except with additional precautions in protecting the fractions from laboratory light during the isolation processes (Table 10). The conclusions of trial 3 agreed with those of trial 2. These spiking experiments showed a maximum value of 0.3-0.4 for the ratio of D-I to total saponins in comparison to a ratio of 0.6-0.8 by cabinet light treatment of crude methanol extracts. Lower ratios would be expected during addition experiments because of reduced concentrations of S-VI found in the HP-20 MeOH isolates. A portion of S-VI had been converted to S-I during the isolation process (because of instability in solution of S-VI). Thus, a reduced amount of S-VI may have been available for photoconversion to D-I compared to S-VI levels expected in minimally-processed crude extracts.

Similar mixing experiments were conducted with Amit chickpea fractions isolated with 60% ethanol as extraction solvent, utilizing the 100% ethanol fraction as a source of S-VI and aqueous ethanol isolates from the HP-20 beads for additions. However, the levels of S-VI (and S-I) were low in the ethanol fraction and consequently any changes in soyasaponin concentrations following the additions were small. In two experiments (prep C and D), the total soyasaponin to internal standard ratios of the HP-20 ethanol fractions (before treatment) were within the range of 2-4, compared to about 10 with methanol as solvent. The reason for low levels of soyasaponins in ethanol extracts was related to their rapid degradation during hot extractions with 60% ethanol. This was unexpected because other researchers have claimed that ethanol had a stabilizing effect on the loss of the maltol group from S-VI isolated from defatted pea flour (19). Despite these problems, the ratio of D-I to internal standard increased from 0.02 (no additions plus 3 days of fluorescent visible light) to 0.2-0.4 on addition of the aqueous ethanol fractions (and 3 days of light treatment). In the experiments with ethanol, addition of the chloroform fraction again did not affect the ratios of soyasaponins to internal standard.

With evidence for involvement of a naturally-occurring photosensitizer in the production of D-I, it was reasonable to further consider the additional evidence in support of riboflavin. Chickpeas and other legume crops are known source of this vitamin and the concentration of riboflavin in chickpeas (typically 0.1-0.3 mg/100 g dry matter or 1-3 ppm) had also been shown to be variety dependent (11, 15). Variety effects have also been documented for cultivated soybeans (66), peas (67) and lentils (12). Environmental factors, in addition to processing and storage conditions, might also result in considerable variations in the vitamin content of legume crop samples (6). Since the influence of visible light on D-I levels appeared to be dependent on the chickpea variety from which the extracts were obtained (see Table 5), it was logical that varying concentrations of riboflavin within the seeds of different varieties could explain at least in part the varying levels of D-I in light-treated extracts. However, the detection of riboflavin in the experimental extracts would be challenging because the extraction process had been developed for recovery of soyasaponins and not the B vitamins. To effectively recover riboflavin from a plant source, the vitamin would first need to be freed from bound proteins and other biological substances by acid hydrolysis of the tissue (13, 14). Flavin mononucleotide (riboflavin 5'-monophosphate, FMN) and flavin adenine dinucleotide (FAD) were common, commercially-available cofactors (coenzymes). Riboflavin can also be converted to lumichrome and other flavins in plant tissues (64). Other studies (20) have examined the photoinduced degradation of flavins including FAD and FMN in detail. Photodegradation studies on sulfamethazine demonstrated that not only riboflavin but also lumichrome and FMN were effective photosensitizers, with the rate of degradation depending on the concentration (51). In other systems, lumichrome was inactive as a photosensitizer, for example in the photodegradation of 2,4-D herbicide in water (18). The standard method for determination of total riboflavin in food utilizes sensitive fluorometric techniques.

To demonstrate the involvement of riboflavin in the chickpea extracts, samples of riboflavin, FMN or FAD were mixed with 80% methanol solutions of S-VI isolated from Amit flour and, after visible light treatment, the conversion to D-I or other products was followed by HPLC (Table 11). Three concentrations of a 30% MeOH isolate were used for comparison (two concentrations were previously employed in Table 10). It was found that the lowest concentration (10 μM) of riboflavin, FMN and FAD led to a clear decrease in S-VI and increase in D-I, paralleling the increased D-I levels found by adding the 30% MeOH isolate. D-I to internal standard ratios were 3.3-4, equivalent to the ratios obtained in tests 3 and 4 with the aqueous methanol additions (see also trial 3 of Table 10). These treatments with riboflavin or its cofactors represented about a four-fold enhancement compared to the light-treated sample of S-VI (test 1) and a 10-fold enhancement compared to untreated samples of S-VI (tests 20 and 21). Higher concentrations of riboflavin, FAD and especially FMN tended to reduce levels of D-I and S-I. This suggested that low concentrations (probably much less than 10 μM) of these photosensitizers in crude chickpea extracts would contribute to the enhanced production of D-I. In other photosensitized systems, riboflavin has been shown to act at low concentrations (69) and acts as a natural dye-sensitizer present in natural waters (72).

Addition of 10, 50 or 100 μM of bergapten, a common psoralen (furocoumarin) photosensitizer activated by long wavelength ultraviolet light (5), did not promote significant degradation of S-VI (tests 14-16). Mixtures containing riboflavin and 30% MeOH (test 17), bergapten and 30% MeOH (test 18) or riboflavin, bergapten and 30% MeOH (test 19) gave similar results.

Figure 7:
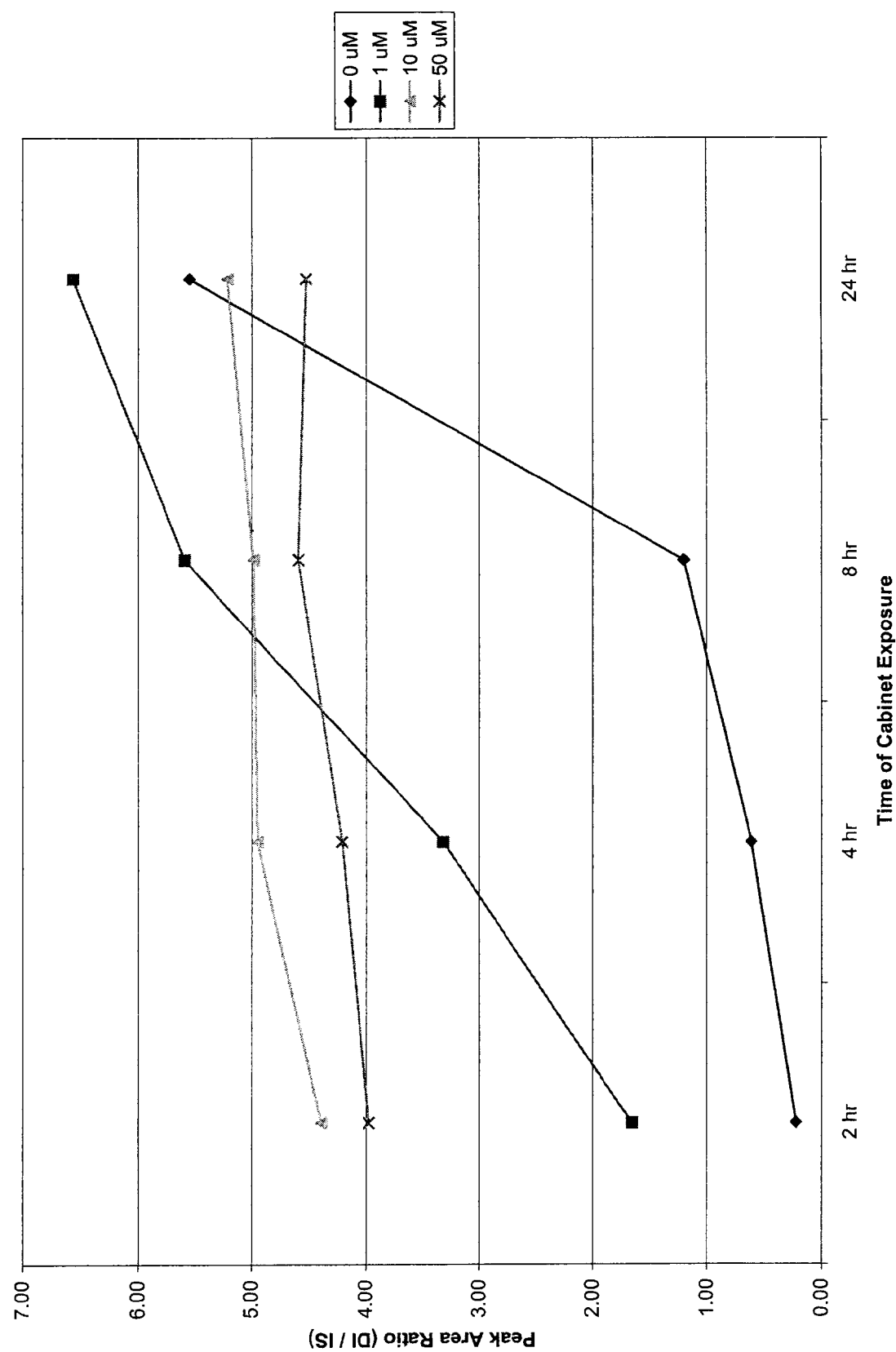
FIG. 7 shows the HPLC/ELSD peak area ratio of D-I to internal standard vs. time. Raw flour samples (1 g) of commercial Amit chickpeas were each extracted at room temperature with 4 ml of 80% methanol (containing 0, 1, 10 or 50 μM riboflavin) during 1 hour. After centrifugation, the supernatants were placed in a cabinet equipped with Cool White visible fluorescent lights (Controlled Environment Chamber, Hoffman Manufacturing, Inc., model SG2-22) for the specified times and then the supernatants were evaporated by N-Evap and Savant apparatus. The residues that remained were redissolved in 80% methanol (3 ml) containing α-hederin (0.25 mg/ml) and syringe filtered (0.45 µm) before HPLC analysis.

Since most of the visible light treatments had been for 2 days, shorter illumination times were examined using Amit chickpea flour extracted with concentrations of added riboflavin ranging from 0-50 μM (FIG. 7). Although sensitivity limitations and potential interferences were apparent, these experiments were performed without sample cleanup before HPLC. Examination of the D-I to internal standard ratios showed the production of D-I increased over 24 hours. A linear increase in D-I occurred with 1 μM, whereas, with no addition of riboflavin, a rapid increase was observed between 8 and 24 hours. Riboflavin at 10 and 50 μM gave relatively flat lines (ratios of 4-5) over the duration of the experiment. It was apparent that intermediate ratios of 4-5 could be realized after about 2 hours with high riboflavin levels but at least a 24 hour cabinet light treatment was required with the 1 μM addition to obtain high concentrations of D-I. The previous treatments of 48 hours were reasonable for unfortified Amit chickpea flour. S-I ratios paralleled those of D-I. As expected, S-VI disappeared gradually during the unfortified and 1 μM treatments whereas this soyasaponin was always below the HPLC detection limit in the experiments with riboflavin at 10 and 50 μM.

It was also important to determine if the addition of riboflavin was capable of enhancing the production of D-I in extracts from other legumes. Flours of a desi chickpea, a kabuli chickpea and two green pea varieties were chosen, examining the soyasaponin ratios after 48 hours of visible light treatment, with riboflavin added at three concentrations (Table 12). CDC Desiray and CDC Frontier gave highest levels of D-I after 1 μM treatments. In the latter variety, the peak area ratio of D-I to internal standard was high (8.9) after riboflavin treatment. This ratio was also obtained with a sample of Amit flour processed with 10 μM riboflavin (data not shown). Higher riboflavin concentrations reduced the ratio of D-I, which was similar to previous findings with semi-purified extracts from Amit chickpeas (Table 11). S-I levels increased in parallel with added riboflavin in flour of CDC Frontier. On the other hand, the highest D-I to internal standard ratios (2.2-3) were found with 10 or 50 μM riboflavin treatments in flours of the green pea varieties. These values represent a 20-30 fold enhancement in D-I levels, compared to visible light treatments without addition of riboflavin (Table 6).

Without wishing to be bound by theory or limiting in any manner, it is reasonable to believe that riboflavin, a natural pigment present in low concentrations in most living cells, acts as a photosensitizer in the photodegradation of S-VI extracted from legume seeds. Good concentrations for production of D-I from kabuli and desi chickpea extracts in 80% methanol were in the range of 1-10 μM, excluding endogenous riboflavin extracted from the seed. Some chickpea varieties such as Amit probably had elevated endogenous levels of riboflavin and sufficient photosensitizer, perhaps in an unidentified or unknown form, was extracted from the flour with 80% methanol. Consequently, addition of riboflavin was not required, provided the cabinet light treatment was of sufficient duration (ca. 48 hours). Defatted soybean flour also gave high levels of D-I without riboflavin treatment. On the other hand, added riboflavin concentrations of 10-50 μM enhanced the formation of D-I in illuminated green pea extracts, probably because the samples of these varieties had low natural levels of the photosensitizer or the riboflavin (or another active form of riboflavin) was ineffectively extracted. Enhancements in D-I levels can also be expected in other species rich in S-VI especially if competitive S-I levels in illuminated extracts remain relatively low as shown here for chickpea.

Example 7

Other Components

It was of interest to examine by LC/MS the Diaion HP-20 fractions from chickpeas to attempt to identify some additional components present in these fractions (major components were of course S-I, S-VI and occasionally D-I). We chose to analyze initially the Diaion HP-20 methanol extracts from seeds of desi and kabuli types (Table 1) in addition to methanolic fractions obtained from green leaves and dry leaves of desi plants (Table 13). After the samples were analyzed by LC/MS and a total ion chromatogram obtained, selected ion chromatograms were evaluated after selecting specific quasimolecular ions (MH+) for probable chickpea components previously described in the literature. The background-subtracted mass spectra of these and other potential components were also obtained. Observations on the number of probable MH+ ions helped to assess the homogeneity of the LC components. Three reference soyasaponins (S-I, MH+943; S-I, MH+ 913; S-II, MH+ 797) and four flavonoids (biochanin A, MH+ 285; biochanin B, MH+ 269; ononin, MH+ 431; sissotrin, MH+ 447) were available from commercial sources (Indofine and Chromadex) to aid with this investigation. Experimental samples of S-I, S-VI and D-I were also available during LC/MS. All ten of these reference compounds gave a strong MH+ ion under positive ion electrospray conditions.

As shown in Table 13, mass spectral evidence was obtained to support the presence of three saponins (in addition to D-I) as minor components of Diaion HP-20 MeOH extracts from all seed samples. The identity of S-III, which was known to occur in soybeans, was confirmed by the availability of an authentic sample. The components with quasimolecular ions at m/z 1252 and 1268 were tentatively identified as 22-O-diglycosides of S-I (abbreviated as 22-gr S-1 and 22-gg S-I, FIG. 8) based on the molecular mass of the same glycosides isolated from soybean and clover species. These seed saponins, not previously reported in chickpeas, were undetectable in leaf extracts. In fact, the major saponins (including D-I) were not found in quantity in leaf extracts. It appeared that S-I may have been present in trace quantities in extracts from dry chickpea leaves. It was possible that other minor seed components with molecular masses of 957, 1029, 1083, 1085, 1098, 1105 and 1237 Da were additional naturally-occurring saponins of this legume since the pea, Adzuki bean, French bean and alfalfa were known to possess glycosides of 12-oleanene-3,22,12-triol (soyasapogenol B) corresponding in mass to one or more of these components.

Figure 8:
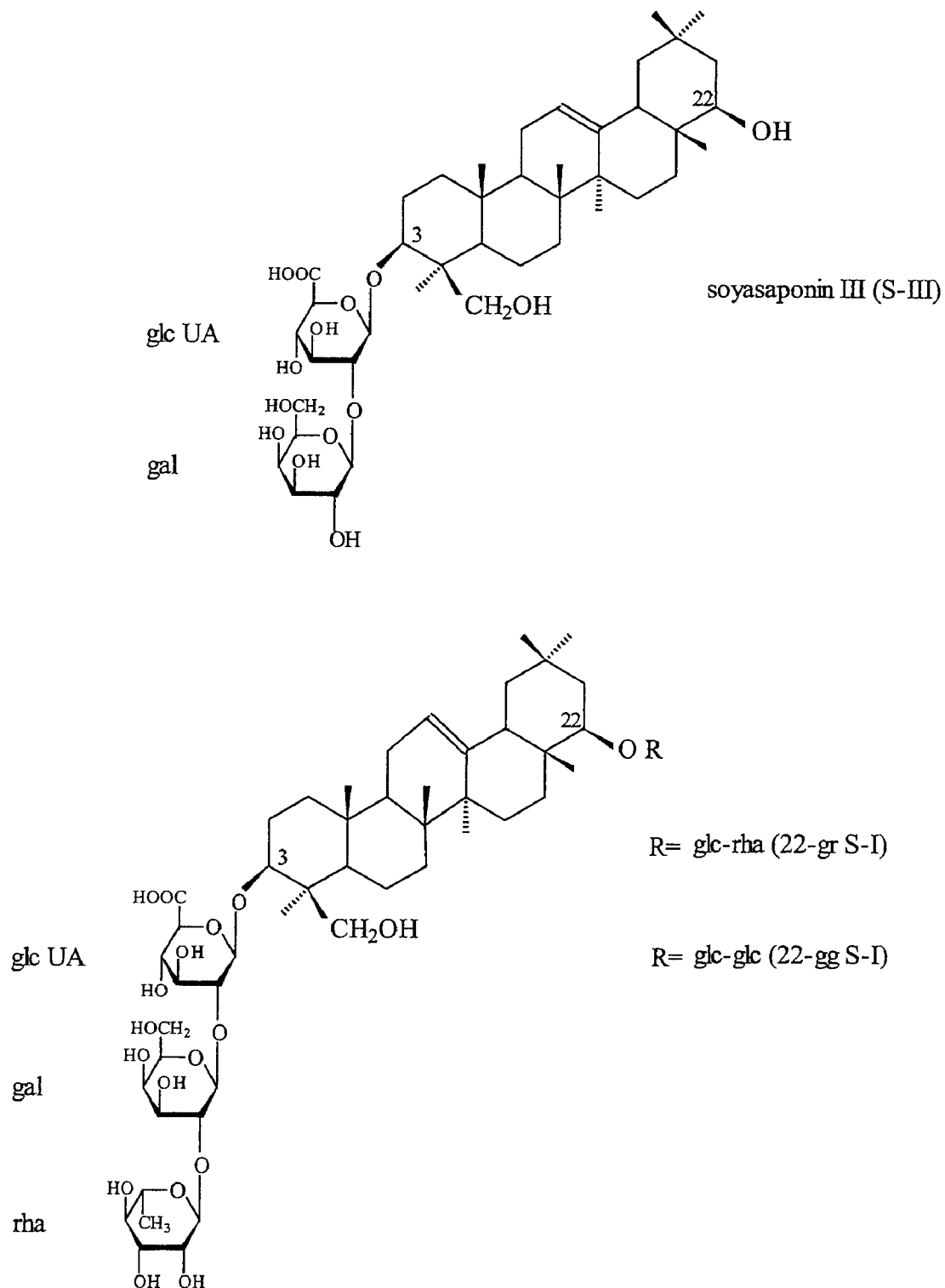
FIG. 8 shows structures of minor components identified or tentatively identified in chickpea extracts.
Figure 8:
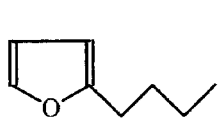
Figure 8:
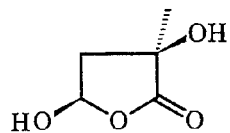
Figure 8:
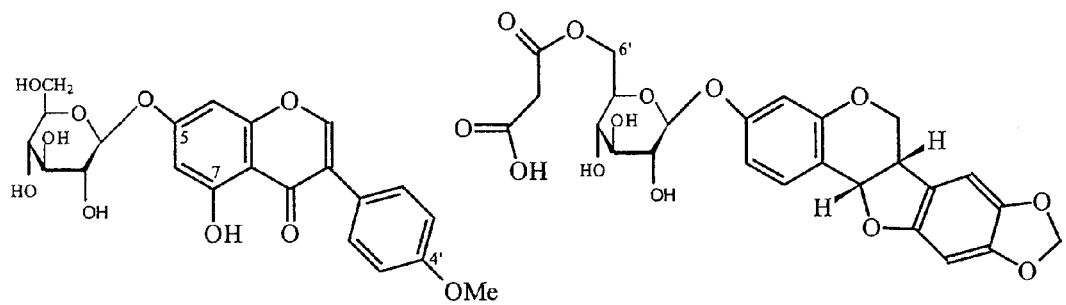
Figure 8:
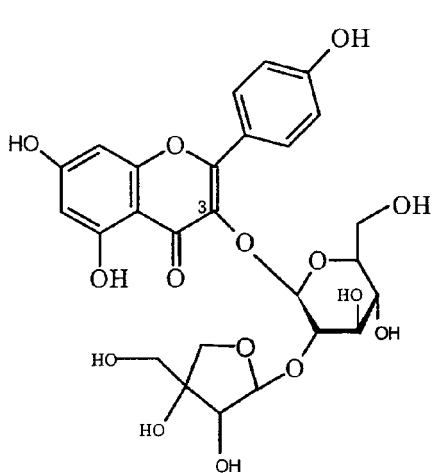
Figure 8:
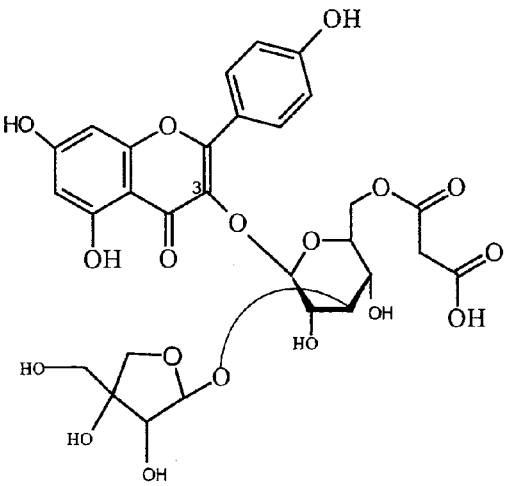

It was interesting to find six additional minor components in HP-20 MeOH extracts that provided a match in molecular mass with previously-identified compounds from chickpeas (middle column of Table 13). These natural products possessed a furan, dihydrofuran or pyran nucleus (FIG. 8). The furan derivatives, 2-bf and 4,5-df, gave relatively weak signals for their quasimolecular ions at m/z 125 and 133, so these materials were difficult to detect with certainty in most extracts. Quasimolecular ions at m/z 205, 217, 247, 295 and 493 (right column of Table 13) could correspond to additional furan (or pyran) derivatives that have been described in the natural product literature (but not associated with the chickpea literature).

Two chickpea components with quasimolecular ions at m/z 447 and 533 were always found in both seed and leaf extracts. The former was readily identified as sissotrin, a commercially-available isoflavone. The other component was tentatively identified as 6'-malonyltrifolirhizin (6-mt), the chickpea glucoside derived from maackiain. Components with weaker quasimolecular ions at m/z 581 and 667 were found in seed extracts. They were tentatively identified as complex kaempferol 3-diglycosides, previously reported to occur in chickpea foliage and abbreviated in FIG. 8 as kag and kamg respectively.

During LC/MS analysis, the appearance at 10 minutes of a weak quasimolecular ion at m/z 285 suggested the presence of biochanin A (284 Da) in seed extracts but the reference sample of this isoflavone eluted with a longer retention time (27.4 minutes). Also, biochanin B (formononetin) or the 7-glucoside (ononin) could not be detected in the experimental extracts. Neither could umbelliferone or scopoletin be detected with certainty. A weak ion at m/z 312 was found (at 5.2 minutes) in most of the seed extracts. This might be attributed to biochanin C, previously isolated from chickpea seeds with a reported molecular mass (311 Da) but with an unknown structure.

Although the Diaion HP-20 MeOH extracts from chickpea seeds have been shown to exist as complex mixtures, composed of 3 major saponins plus at least 25 minor components, not all of the compounds previously reported would be expected to occur in these particular extracts. The extraction and clean-up processes were naturally designed for isolation of the soyasaponins of interest, particularly D-I. Some of the natural products may have been removed during the chloroform defatting step or may have been insoluble in the 80% methanol extraction solvent. Other products may have decomposed or evaporated during the extraction and analysis steps or during brief exposure to light. It was also possible that other products of the crude mixture were lost in aqueous alcohol washes of the Diaion HP-20 beads. In this regard, the aqueous methanol and ethanol washes from a few of the crude chickpea extracts were examined by LC/MS to characterize by mass spectrometry the main components (Table 14). Further mass spectral collision-induced dissociation experiments on five of these components (with MH+ of m/z 205, 217, 247, 295 and 493) suggested that the components were related to coumarin (146 Da), acetylcoumarin (188 Da) or psoralen (186 Da). Prominent daughter ions from MH+ 205 were found at m/z 188, 146, 118; MH+ 217 gave daughter ions at m/z 171 and 144; MH+ 247 gave daughter ions at m/z 188, 146 and 118; MH+ 295 gave daughter ions at m/z 186, 166 and 120; MH+ 493 gave daughter ions at m/z 247 and 188. The small component of MH+ 312 gave a daughter ion at m/z 166, suggesting that this component may also be a coumarin derivative (but with a substituent containing a nitrogen atom).

Mass spectroscopy analysis of extracts did not unambiguously identify riboflavin (at m/z 377), lumiflavin (m/z 257), riboflavin 4',5'-cyclic phosphate (m/z 439), FMN (m/z 457) or FAD (m/z 786) in extract samples. Most of the samples, however, gave a weak signal at m/z 243, corresponding in mass to lumichrome, a riboflavin degradation product. Further, riboflavin and its cofactors were also below the detection limit in aqueous alcohol washes (Table 14) suggesting that the recovery of riboflavin by extraction with methanol (or ethanol) was very low.

With regard to the influence of light treatment on the distribution of chickpea components, LC/MS showed that unknown components with MH+ of m/z 1084, 1086, 1099 and 1106 (right column of Table 13) were undetectable (and therefore photolabile), including in the extracts exposed to UVA, UVC and sunlight. Ions corresponding to 958 and 1043 were weak in light-treated extracts. Of course, S-VI at m/z 1069 was also reduced or absent. In addition to D-I, the component with MH+ at m/z 1030 had increased in concentration (see FIG. 6). The coumarin-like materials detected in quantity in aqueous alcohol extracts were present in both untreated and light-treated extracts (Table 14). Phospholipids of the lysolecithin type, with retention times of 34-36 minutes and MH+ of m/z 496, 520 and 522, were found in all Diaion HP-20 and chloroform extracts (61).

REFERENCES

1. Addy, M. E. Pharmacological actions of *Desmodium adscendens*, a Ghanian medicinal plant. *Discovery and Innovation* 1993, 5, 205-210.
2. Ahmad, I.; Fasihullah, Q.; Vaid, F. H. Effect of light intensity and wavelengths on photodegradation reactions of riboflavin in aqueous solution. J. Photochem. Photobiol. B. 2006, 82, 21-27.
3. Bleton, J.; Mejanelle, P.; Sansoulet, J.; Goursaud, S.; Tchapla, A. Characterization of neutral sugars and uronic acids after methanolysis and trimethylsilylation for recognition of plant gums. *J Chromatogr. A* 1996, 720, 27-49.
4. Bodnaryk, R. P.; Fields, P. G.; Xie, Y.; Fulcher, K. A. Insecticidal factor from field peas. U.S. Pat. No. 5,955,082. 1999.
5. Caffieri, S. Furocoumarin photolysis: chemical and biological aspects. Photochem. Photobiol. Sci. 2002, 1, 149-157.
6. Chavan, U. D.; Shahidi, F.; Bal, A. K.; McKenzie, D. B. Physico-chemical properties and nutrient composition of beach pea (*Lathyrus maritimus* L.). Food Chemistry 1999, 66, 43-50.
7. Choe, E.; Huang, R.; Min, D. B. Chemical reactions and stability of riboflavin in foods. Journal of Food Science 2005, 70, R28-R36.
8. Ding, Y.; Takeshita, T.; Yokoyama, K.; Kinjo, J.; Nohara, T. Triterpenoid glycosides from Sophorae subprostratae Radix. *Chem. Pharm. Bull.* 1992, 40, 139-142.
9. Dixon, R. A.; Sumner, L. W. Legume natural products: Understanding and manipulating complex pathways for human and animal health. *Plant Physiology* 2003, 131, 878-885.
10. Doco, T.; O'Neill, M. A.; Pellerin, P. Determination of the neutral and acidic glycosyl-residue compositions of plant polysaccharides by GC-EI-MS analysis of the trimethylsilyl methyl glycoside derivatives. *Carbohydrate Polymers* 2001, 46, 249-259.
11. Dodok, L.; Ali, M. A.; Hozova, B.; Halasova, G.; Polacek, I. Importance and utilization of chickpea in cereal technology. Acta Alimentaria 1993, 22, 119-129.
12. El-Nahry, F. I.; Mourad, F. E.; Khalik, S. M. A.; Bassily, N. S. Chemical composition and protein quality of lentils (Lens) consumed in Egypt. Qual. Plant Foods Hum. Nutr. 1980, 30, 87-95.
13. Esteve, M. J.; Farre, R.; Frigola, A.; Garcia-Cantabella, J. M. Simultaneous determination of thiamin and riboflavin in mushrooms by liquid chromatography. J. Agric. Food Chem. 2001, 49, 1450-1454.
14. Fernando, S. M.; Murphy, P. A. HPLC determination of thiamin and riboflavin in soybeans and tofu. J. Agric. Food Chem. 1990, 38, 163-167.
15. Gaborcik, N.; Uherova, R. Variability of chemical composition in chickpea (*Cicer arietinum* L.) Cultivars. III. Content of some vitamins of the B-group. Polnohospodarstvo 1997, 43, 503-507.
16. Ganzera, M.; Stuppner, H.; Khan, I. A. Simultaneous determination of saponins and isoflavones in soybean (*Glycine max* L.) by reversed-phase liquid chromatography with evaporative light-scattering and ultraviolet detection. *Journal of AOAC International.* 2004, 87, 1189-1194.
17. Garcia, N. A.; Criado, S. N.; Massad, W. A. Riboflavin as a visible-light-sensitizer in the aerobic photodegradation of ophthalmic and sympathomimetic drugs. Flavins: Photochemistry and photobiology; comprehensive Series in Photochemical & Photobiological Sciences 2006, 6, 61-82.
18. Harrison, S. K.; Venkatesh, R. Light regime, riboflavin, and pH effects on 2,4-D photodegradation in water. Journal of Environmental Science and Health. Part B. Pesticides, Food Contaminants, and Agricultural Wastes 1999, 34, 469-489.

19. Heng, L.; Vincken, J. P.; Hoppe, K.; van Koningsveld G. A.; Decroos, K.; Gruppen, H.; van Boekel, M. A. J. S.; Voragen, A. G. J. Stability of pea DDMP saponin and the mechanism of its decomposition. *Food Chemistry.* 2006, 99, 326-334.
20. Holzer, W.; Shirdel, J.; Zirak, P.; Penzkofer, A.; Hegemann, P.; Deutzmann, R.; Hochmuth, E. Photo-induced degradation of some flavins in aqueous solution. Chemical Physics 2005, 308, 69-78.
21. Hou, X.; Fields, P.; Taylor, W. Combination of protein-rich pea flour and pea extract with insecticides and enzyme inhibitors for control of stored-product beetles. *The Canadian Entomologist* 2004, 136, 581-590.
22. Hu, J.; Lee, S.; Hendrich, S.; Murphy, P. A. Quantification of the group B soyasaponins by high-performance liquid chromatography. *J. Agric. Food Chem.* 2002, 50, 2587-2594.
23. Huang, R.; Kim, H. J.; Min, D. B. Photosensitizing effect of riboflavin, lumiflavin, and lumichrome on the generation of volatiles in soy milk. J. Agric. Food Chem. 2006, 54, 2359-2364.
24. Ireland, P. A.; Dziedzic, S. Z. Saponins and sapogenins of chick pea, haricot bean and red kidney bean. *Food Chemistry* 1987, 23, 105-116.
25. Itoh, T.; Umekawa, H.; Furuichi, Y. Potential ability of hot water adzuki (*Vigna angularis*) extracts to inhibit the adhesion, invasion, and metastasis of murine B16 melanoma cells. Biosci. Biotechnol. Biochem. 2005, 69, 448-454.
26. Jarvis, A. P.; Johnson, S.; Morgan, E. D.; Simmonds, M. S. J.; Blaney, W. M. Photooxidation of nimbin and salannin, tetranortriterpenoids from the neem tree (*Azadirachta indica*). *Journal of Chemical Ecology.* 1997, 23, 2841-2860.
27. Jood, S.; Chauhan, B. M.; Kapoor, A. C. Saponin content of chickpeas and black gram: varietal differences and effects of processing and cooking methods. *J. Sci. Food Agric.* 1986, 37, 1121-1124.
28. Kao, T. H.; Lu, Y. F.; Chen, B. H. Preparative column chromatography of four groups of isoflavones from soybean cake. European Food Research and Technology. 2005, 221, 459-465.
29. Kerem, Z.; German-Shashoua, H.; Yarden, O. Microwave-assisted extraction of bioactive saponins from chickpea (*Cicer arietinum* L.). *J Sci. Food Agric.* 2005, 85, 406-412.
30. Kinjo, J.; Kishida, F.; Watanabe, K.; Hashimoto, F.; Nohara, T. Five new triterpene glycosides from Russell lupine. *Chem. Pharm. Bull.* 1994, 42, 1874-1878.
31. Kitagawa, I.; Taniyama, T.; Hong, W. W.; Hori, K.; Yoshikawa, M. Saponin and sapogenol. XLV. Structures of kaikasaponins I, II, and III from Sophorae Flos, the buds of *Sophora japonica* L. *Yakugaku Zasshi* 1988, 108, 538-546.
32. Kitagawa, I.; Taniyama, T.; Murakami, T.; Yoshihara, M.; Yoshikawa, M. Saponin and sapogenol. XLVI. On the constituents in aerial part of American alfalfa, *Medicago sativa* L. The structure of dehydrosoyasaponin I. *Yakugaku Zasshi* 1988, 108, 547-554.
33. Konoshima, T.; Kozuka, M.; Haruna, M.; Ito, K. Constituents of leguminous plants, XIII. New triterpenoid saponins from *Wistaria brachybotrys. J. Nat. Prod.* 1991, 54, 830-836.
34. Kubo, T.; Hamada, S.; Nohara, T.; Wang, Z.; Hirayama, H.; Ikegami, K.; Yasukawa, K.; Takido, M. Study on the Constituents of *Desmodium styracifolium. Chem. Pharm. Bull.* 1989, 37, 2229-2231.
35. Kudou, S.; Tonomura, M.; Tsukamoto, C.; Shirnoyamada, M.; Uchida, T.; Okubo, K. Isolation and structural elucidation of the major genuine soybean saponin. *Biosci. Biotech. Biochem.* 1992, 56, 142-143.
36. Lacaille-Dubois, M. A.; Wagner, H. A review of the biological and pharmacological activities of saponins. *Phytomedicine* 1996, 2, 363-386.
37. Mahato, S. B. Triterpenoid saponins from *Medicago hispida. Phytochemistry* 1991, 30, 3389-3393.
38. Marx, S. O.; Zakarov, S. I. Use of rottlerin and its derivatives as activators of BK channel for therapy of hypertension and related disorders. WO 2006060196. Published Jun. 8, 2006.
39. Massiot, G.; Dijoux, G. M.; Lavaud, C. Saponins and artifacts. In G. R. Waller and K. Kamasaki (Eds.). *Saponins Used in Food and Agriculture*, Plenum Press, New York, 1996, pp. 183-192.
40. Massiot, G.; Lavaud, C.; Benkhaled, M.; Le Men-Olivier, L. Soyasaponin VI, a new maltol conjugate from alfalfa and soybean *J Nat. Prod.* 1992, 55, 1339-1342.
41. McManus, O. B.; Harris, G. H.; Giangiacomo, K. M.; Feigenbaum, P.; Reuben, J. P.; Addy, M. E.; Burka, J. F.; Kaczorowski, G. J.; Garcia, M. L. An activator of calcium-dependent potassium channels isolated from a medicinal herb. *Biochemistry* 1993, 32, 6128-6133.
42. McManus, O. B.; Helms, L. M. H.; Pallanck, L.; Ganetzky, B.; Swanson, R.; Leonard, R. J. Functional role of the subunit of high conductance calcium-activated potassium channels. *Neuron* 1995, 14, 645-650.
43. Miyao, H.; Sakai, Y.; Takeshita, T.; Kinjo, J.; Nohara, T. Triterpene saponins from *Abrus cantoniensis* (Leguminosae). I. Isolation and characterization of four new saponins and a new sapogenol. *Chem. Pharm. Bull.* 1996, 44, 1222-1227.
44. Mohamed, K. M.; Ohtani, K.; Kasai, R.; Yamasaki, K. Oleanene glycosides from seeds of *Trifolium alexandrinum. Phytochemistry* 1995, 40, 1237-1242.
45. Murakami, T.; Kohno, K.; Matsuda, H.; Yoshikawa, M. Medicinal foodstuffs. XXII. Structures of oleanane-type triterpene oligoglycosides, pisumsaponins I and II, and kaurane-type diterpene oligoglycosides, pisumosides A and B, from green peas, the immature seeds of *Pisum sativum* L. *Chem. Pharm. Bull.* 2001, 49, 73-77.
46. Nardi, A.; Calderone, V.; Chemconi, S.; Morelli, I. Natural modulators of large-conductance calcium-activated potassium channels. *Planta Med* 2003, 69, 885-892.
47. Nardi, A.; Calderone, V.; Olesen, S. P. Potassium channel openers: The case of BK channel activators. *Letters in Drug Design and Discovery.* 2006, 3, 210-218.
48. Okubo, K.; Yoshiki, Y. Effect of DDMP saponin on the flavor and color of soybean foods. *Kenkyuka Kaishi* 1994, 15, 36-40.
49. Okubo, K.; Yoshiki, Y. Oxygen-radical-scavenging activity of DDMP-conjugated saponins and physiological role in leguminous plant. In G. R. Waller and K. Kamasaki (Eds.). *Saponins Used in Food and Agriculture*, Plenum Press, New York, 1996, pp. 141-154.
50. Okubo, K.; Yoshiki, Y.; Okuda, K.; Sugihara, T.; Tsukamoto, C.; Hoshikawa, K. DDMP-conjugated saponin (soyasaponin g) isolated from American groundnut (*Apio americana*). *Biosci. Biotech. Biochem.* 1994, 58, 2248-2250.
51. Parks, O. Photodegradation of sulfa drugs by fluorescent light. JAOAC 1985, 68, 1232-1234.
52. Price, K. R.; Fenwick, G. R. The chemistry and biological significance of saponins in foods and feeding stuffs. *CRC Crit. Rev. Food Sci. Nutr.* 1987, 26, 27-135.
53. Ruiz, R. G.; Price, K. R.; Arthur, A. E.; Rose, M. E.; Rhodes, M. J. C.; Fenwick, R. G. Effect of soaking and 53. cooking on the saponin content and composition of chickpeas (*Cicer arietinum*) and lentils (*Lens culinaris*). J. Agric. Food Chem. 1996, 44, 1526-1530.
54. Ruiz, R. G.; Price, K. R.; Rose, M. E.; Arthur, A. E.; Petterson, D. S.; Fenwick, G. R. The effect of cultivar and environment on saponin content of Australian sweet lupin seed. J. Sci. Food Agric. 1995, 69, 347-351.
55. Rupasinghe, H. P. V.; Jackson, C.-J. C.; Poysa, V.; Berardo, C. D.; Bewley, J. D.; Jenkinson, J. Soyasapogenol A and B distribution in soybean (*Glycine max* L. Merr.) in relation to seed physiology, genetic variability, and growing location. J. Agric. Food Chem. 2003, 51, 5888-5894.
56. Shiraiwa, M.; Harada, K.; Okubo, K. Composition and structure of "group B saponin" in soybean seed. Agric. Food Chem. 1991, 55, 911-917.
57. Sun, R. Q.; Jia, Z. J. Saponins from *Oxytropis glabra*. Phytochemistry 1990, 29, 2032-2034.
58. Sun, R. Q.; Jia, Z. J.; Cheng, D. L. Three saponins from *Oxytropis* species. Phytochemistry 1991, 30, 2707-2709.
59. Taylor W. G.; Fields, P. G.; Sutherland, D. H. Canadian Patent application 2499102. Insecticidal extract from legume plants and method of preparing the same. Published Sep. 24, 2006.
60. Taylor W. G.; Fields, P. G.; Sutherland, D. H. United States Patent application 20060216367. Insecticidal extract from legume plants and method of preparing the same. Published Sep. 28, 2006.
61. Taylor, W. G.; Fields, P. G.; Sutherland, D. H. Insecticidal components from field pea extracts. Soyasaponins and lysolecithins. J. Agric. Food Chem. 2004, 52, 7484-7490.
62. Taylor, W. G.; Fields, P. G.; Sutherland, D. H. Fractionation of lentil seeds (*Lens Culinaris Medik*) for insecticidal and flavonol tetraglycoside components. J. Agric. Food Chem. 2007, 55, 5491-5498.
63. Taylor, W. G.; Sutherland, D. H.; Olson, D. J. H.; Ross A. R. S.; Fields, P. G. Insecticidal components from field pea extracts. Sequences of some variants of pea albumin 1b. J. Agric. Food Chem. 2004, 52, 7499-7506.
64. Treadwell, G. E.; Metzler, D. E. Photoconversion of riboflavin to lumichrome in plant tissues. Plant Physiol. 1972, 49, 991-993.
65. Tsurumi, S.; Takagi, T.; Hashimoto, T. A γ-pyronyl-triterpenoid saponin from *Pisum sativum*. Phytochemistry 1992, 31, 2435-2438.
66. Vedrina-Dragojevic, I.; Sebecic, B.; Balint, L. Variability of thiamine, riboflavin and naicin content in soybean seed. Die Nahrung 1989, 33, 1017-1019.
67. Vidal-Valverde, C.; Frias, J.; Hernandez, A.; Martin-Alvarez, P. J.; Sierra, I.; Rodriguez, C.; Blazquez, I.; Vicente, G. Assessment of nutritional compounds and antinutritional factors in pea (*Pisum sativum*) seeds. J. Sci. Food Agric. 2003, 83, 298-306.
68. Wold, J. P.; Bro, R.; Veberg, A.; Lundby, F.; Nilsen, A. N.; Moan, J. Active photosensitizers in butter detected by fluorescence spectroscopy and multivariate curve resolution. J. Agric. Food Chem. 2006, 54, 10197-10204.
69. Yang, X.; Zhao, X.; Hwang, H. M. Phototransformation of 2,4,6-trinitrotoluene: Sensitized by riboflavin under different irradiation spectral range. Journal of Hazardous Materials 2007, 143, 271-276.
70. Yoshikawa, M.; Shimada, H.; Komatsu, H.; Sakurama, T.; Nishida, N.; Yamahara, J.; Shimoda, H.; Matsuda, H.; Tani, T. Medicinal foodstuffs. VI. Histamine release inhibitors from kidney bean, the seeds of *Phaseolis vulgaris* L.: chemical structures of sandosaponins A and B. Chem. Pharm. Bull. 1997, 45, 877-882.
71. Yoshiki, Y.; Takagi, S.; Watanabe, N.; Okubo, K. Fractionation of soybean functional glycosides from soy-waste based on the chemical reaction of soyasaponin β g. Food Chemistry. 2005, 93, 591-597.
72. Zhao, X.; Hu, X.; Hwang, H. M. Effects of riboflavin on the phototransformation of benzo[a]pyrene. Chemosphere 2006, 63, 1116-1123.

All citations are hereby incorporated by reference.

The present invention has been described with regard to one or more embodiments. However, it will be apparent to persons skilled in the art that a number of variations and modifications can be made without departing from the scope of the invention as defined in the claims.

TABLE 1

Relative concentrations of chickpea soyasaponins and yields of saponin-enriched fractions obtained by Diaion HP-20 bead technology.

| Variety | S-I[a] | D-I[b] | S-VI[c] | total soyasaponins | yield (%) | D-I/(S-I + D-I + S-VI) |
|---|---|---|---|---|---|---|
| Desi | | | | | | |
| CDC Anna | 2.8 | 0.1 | 5.0 | 7.9 | 1.24[d] | 0.01 |
| CDC Cabri | 2.9 | 0.2 | 11.7 | 14.9 | 0.39 | 0.01 |
| CDC Desiray | 0.9 | 0.05 | 12.5 | 13.4 | 0.38 | 0.004 |
| CDC Nika | 0.8 | 0.05 | 5.0 | 5.9 | 0.58 | 0.008 |
| Myles | 3.2 | 0.2 | 7.4 | 10.8 | 0.51 | 0.02 |
| Chickpea flour | 6.7 | 0.2 | 1.4 | 8.3 | 0.40 | 0.02 |
| Kabuli | | | | | | |
| Amit (B-90) | 6.3 | 3.0 | 0.9 | 10.2 | 0.32 | 0.29 |
| Amit (B-90)[e] | 0.7 | <0.02 | 5.8 | 6.5 | 0.47 | <0.003 |
| CDC Chi Chi | 1.9 | 2.4 | 2.2 | 6.5 | 0.34 | 0.37 |
| CDC Chico | 3.4 | 2.1 | 1.2 | 6.6 | 0.32 | 0.32 |
| CDC Diva | 1.0 | 0.1 | 2.2 | 3.3 | 0.41 | 0.03 |
| CDC Frontier | 2.2 | 0.05 | 11.3 | 13.5 | 0.61[d] | 0.004 |
| CDC Verano | 6.5 | 0.3 | 0.6 | 7.4 | 0.46 | 0.04 |
| CDC Xena | 1.5 | 0.2 | 3.0 | 4.6 | 0.20 | 0.04 |
| CDC Yuma | 2.9 | 1.6 | 8.6 | 13.2 | 0.32 | 0.12 |
| Dwelley | 1.3 | 0.9 | 0.4 | 2.6 | 0.24 | 0.35 |
| Sanford | 2.9 | 2.3 | 1.2 | 6.4 | 0.37 | 0.36 |
| Sanford[e] | 0.3 | <0.02 | 1.7 | 2.1 | 0.35 | <0.01 |
| field pea flour | 1.7 | 0.04 | 2.9 | 4.6 | 1.1[d] | 0.009 |

[a]The data in this column represents the HPLC peak area of soyasaponin I (retention time 21.5 min) divided by the peak area for α-hederin (26.3 min). All HPLC solutions were prepared in 80% methanol at concentrations of 0.25 mg/mL (α-hederin internal standard) and 8 mg/mL (HP-20 MeOH fractions).
[b]The data in this column represents the peak area of dehydrosoyasaponin I (retention time 24.9 min) divided by the peak area for α-hederin.
[c]The data in this column represents the peak area of soyasaponin VI (retention time 25.6 min) divided by the peak area for α-hederin.
[d]These samples probably were not completely dry.
[e]Greenhouse-grown seed.

TABLE 2

Yield comparison of dehydrosoyasaponin I isolated from various legume species.

| Species | Country of Origin | Plant part (amount) | Extraction | Derivatization | Purification | Yield | Reference |
|---|---|---|---|---|---|---|---|
| Desmodium styracifolium | China | whole plants (1 kg) | MeOH, water-saturated n-BuOH | methyl esters, for spectral identification | Sephadex LH-20, silica | 0.0057%[a] | Kubo et al (34) |
| Wistaria brachybotrys | Japan | knots (2.5 kg) | 80% MeOH, water-saturated n-BuOH | methyl esters, for gel permeation chromatography | silica, preparative HPLC (GPC column) | 0.0016%[a] | Konoshima et al (33) |
| Sophora subprostrata | China | roots (8 kg) | MeOH, 40% MeOH | methyl esters, for silica chromatography | Diaion HP-20, Sephadex LH-20, C-18 silica, silica | 0.00064%[a] | Ding et al (8) |
| Desmodium adscendens | unspecified | leaves (0.175 kg) | water, water-saturated n-BuOH | | Sephadex LH-20 C-18 silica counter current chromatography C-18 HPLC | 0.0022%[a] | McManus et al (41) |
| Lupinus polyphyllus × Lupinus arboreus hybrid | Japan | roots (4.56 kg) | MeOH, 80% MeOH | | C-18 silica, MCI gel, Sephadex LH-20, silica | 0.0013% | Kinjo et al (30) |
| Trifolium alexandrinum | Egypt | seeds (3 kg) | MeOH, water | methyl esters, for polyamine HPLC | Diaion HP-20 silica, C-18 silica C-18 HPLC, polyamine HPLC | 0.0014% | Mohamed et al (44) |
| Abrus contoniensis | Japan | whole plants (10 kg) | MeOH, 80% MeOH, 40% MeOH | | MCI gel, Sephadex LH-20, C-18 HPLC, silica | 0.0005% | Miyao et al (43) |
| Phaseolus vulgaris | Japan | seeds (10 kg) | MeOH, water, n-BuOH | | silica, C-18 silica, C-18 HPLC | 0.0004% | Yoshikawa et al (70) |
| Pisum sativum | Japan | immature green seeds (4.8 kg) | MeOH, water | | Diaion HP-20, silica, C-18 silica, C-18 HPLC | 0.00091% | Murakami et al (45) |
| Pisum sativum | Canada | commercial flour of yellow pea (0.1 kg) | 80% MeOH | | C-8 silica, silica, polystyrene/divinylbenzene column at pH 10.5 | 0.0015% | Taylor et al (61) |
| Cicer arietinum | Canada | seeds of Amit (0.1 kg) | 80% MeOH | | Diaion HP-20, polystyrene/divinylbenzene column at pH 10.5 | 0.024% | This work |

[a]These yields were calculated here from the reported masses of starting plant material and isolated D-I.

TABLE 3

Influence of storage of 80% methanol extracts on levels of chickpea soyasaponins from CDC Chico flour.[a]

| storage[b] | extraction conditions | S-I | D-I | S-VI | total soyasaponins | D-I/(S-I + D-I + S-VI) |
|---|---|---|---|---|---|---|
| <1 day in laboratory | room temp. 75 min. | 2.5 | 0.09 | 5.4 | 8.0 | 0.01 |
| | reflux 5 min. | 3.6 | 0.1 | 7.2 | 10.9 | 0.009 |
| | reflux 15 min. | 2.6 | 0.04 | 7.5 | 10.1 | 0.004 |
| | reflux 30 min. | 3.0 | 0.07 | 8.5 | 11.6 | 0.006 |
| | reflux 60 min. | 2.5 | 0.06 | 7.1 | 9.7 | 0.006 |
| 7 days in refrigerator | room temp. 75 min. | 1.9 | 0.2 | 3.0 | 5.1 | 0.04 |
| | reflux 5 min. | 2.4 | 0.8 | 5.8 | 8.2 | 0.1 |
| | reflux 15 min. | 1.6 | 0.07 | 4.6 | 6.3 | 0.01 |
| | reflux 30 min. | 3.0 | 0.1 | 7.2 | 10.3 | 0.01 |
| | reflux 60 min. | 3.4 | 0.09 | 6.7 | 10.3 | 0.009 |
| 7 days in laboratory | room temp. 75 min. | 1.5 | 1.9 | 0.2 | 3.5 | 0.54 |
| | reflux 5 min. | 3.5 | 3.5 | 0.4 | 7.5 | 0.47 |
| | reflux 15 min. | 3.7 | 3.1 | 0.7 | 7.5 | 0.41 |
| | reflux 30 min. | 4.0 | 3.1 | 0.8 | 7.9 | 0.39 |
| | reflux 60 min. | 3.8 | 3.0 | 0.8 | 7.6 | 0.40 |

TABLE 3-continued

Influence of storage of 80% methanol extracts on levels of chickpea soyasaponins from CDC Chico flour.[a]

| storage[b] | extraction conditions | S-I | D-I | S-VI | total soyasaponins | D-I/ (S-I + D-I + S-VI) |
|---|---|---|---|---|---|---|
| Chico HP-20 methanol fraction[c] | | 2.8 | 1.4 | 0.2 | 4.4 | 0.32 |

[a]Relative levels were estimated by the HPLC/ELSD method described for Table 1 but with a different ELSD. Crude extracts were further processed during the day of extraction (<1 day) or were stored in 5 ml Pyrex™ glass volumetric flasks before treatment with Diaion HP-20 beads.
[b]The average laboratory temperature was 20.5° C.; refrigerator temperature was 5° C. The laboratory was equipped with fluorescent lights (Sylvania SuperSaver Cool White F40CW/SS 34 watts), the refrigerator had no light. The laboratory has windows along one side.
[c]This reference sample was derived by the 100-gram scale extraction procedure of Table 1 but with Chico flour (1.5 years post-grinding) of similar age as used for 1-gram scale experiments.

TABLE 4

Influence on chickpea soyasaponins levels of four different treatments of crude extracts from CDC Chico flour.[a]

| treatment | S-I | D-I | S-VI | total soyasaponins | (D-I/ S-I + D-I + S-VI) |
|---|---|---|---|---|---|
| regular[b] | 1.2 | 1.4 | <0.05 | 2.6 | 0.54 |
| EDTA[c] | 1.2 | 1.8 | <0.05 | 3.1 | 0.58 |
| amber[d] | 0.8 | 0.2 | 1.2 | 2.2 | 0.09 |
| aluminum foil[e] | 1.1 | 0.06 | 1.8 | 3.0 | 0.02 |

[a]Crude extracts, obtained by extraction of the flour (1 g) at room temperature with 4 ml of 80% methanol followed by centrifugation at 2000 rpm, were stored in 4 ml borosilicate glass vials (Kimble Glass Inc. Part no. 60940-4) equipped with Teflon™ lined screw-caps before treatment with Diaion HP-20 beads. HPLC peak area ratios were obtained as before (Table 1).
[b]This crude extract obtained by extraction with 80% methanol was stored in the laboratory for 7 days.
[c]This crude extract obtained by extraction with 80% methanol containing 0.01% EDTA was stored in the laboratory for 7 days.
[d]This crude extract obtained by extraction with 80% methanol was stored in a 4 ml borosilicate amber vial (Wheaton part no. 224982) in the laboratory for 7 days.
[e]This crude extract obtained by extraction with 80% methanol was stored in a clear glass vial wrapped with aluminum foil in the laboratory for 7 days.

TABLE 5

Relative levels of soyasaponins from extracts of desi and kabuli chickpea, field pea and lentil exposed briefly and for 7 days to ordinary laboratory conditions.[a]

| variety[b] | S-I brief | S-I 7 day | D-I brief | D-I 7 day | S-VI brief | S-VI 7 day | total soyasaponins (D-I + S-I + S-VI ratios) brief | total soyasaponins (D-I + S-I + S-VI ratios) 7 day | D-I to soyasaponin ratio (D-I ratio/D-I + S-I + S-VI ratios) brief | D-I to soyasaponin ratio (D-I ratio/D-I + S-I + S-VI ratios) 7 day | D-I index (D-I ratio × total soyasaponin ratio) brief | D-I index (D-I ratio × total soyasaponin ratio) 7 day | D-I purity index (D-I ratio × % D-I in mixture by HPLC/ELSD peak areas) brief | D-I purity index (D-I ratio × % D-I in mixture by HPLC/ELSD peak areas) 7 day |
|---|---|---|---|---|---|---|---|---|---|---|---|---|---|---|
| desi | | | | | | | | | | | | | | |
| CDC Anna | 0.2 | 0.4 | 0.002 | 0.08 | 2.5 | 1.3 | 2.7 | 1.8 | 0.0008 | 0.05 | 0.006 | 0.1 | <0.0001 | 0.01 |
| CDC Cabri | 1.0 | 1.9 | 0.08 | 1.4 | 2.6 | 1.9 | 4.6 | 5.2 | 0.02 | 0.3 | 0.3 | 7.3 | 0.04 | 12 |
| CDC Desiray | 0.5 | 0.6 | 0.03 | 0.3 | 2.8 | 0.5 | 3.3 | 1.5 | 0.01 | 0.2 | 0.1 | 0.5 | 0.01 | 0.6 |
| CDC Nika | 0.7 | 0.9 | 0.06 | 0.8 | 3.0 | 0.3 | 3.7 | 2.0 | 0.02 | 0.4 | 0.2 | 1.6 | 0.02 | 4.8 |
| Myles | 1.8 | 2.4 | 0.08 | 0.9 | 6.1 | 2.1 | 8.0 | 5.4 | 0.01 | 0.2 | 0.6 | 5.0 | 0.02 | 5.9 |
| chickpea flour | 1.0 | 1.8 | 0.0005 | 0.3 | 3.4 | 1.5 | 4.4 | 3.6 | 0.0001 | 0.1 | 0.002 | 1.1 | <0.0001 | 0.1 |
| kabuli | | | | | | | | | | | | | | |
| Amit (B-90) | 3.2 | 2.7 | 0.3 | 5.0 | 5.9 | 0.0008 | 9.4 | 7.7 | 0.03 | 0.6 | 2.5 | 38.0 | 0.3 | 112 |
| | 3.4[c] | 3.0 | 0.2 | 5.9 | 6.2 | 0.002 | 9.7 | 9.0 | 0.02 | 0.7 | 1.5 | 53.1 | 0.1 | 83 |
| | 3.1[c,d] | 4.4 | 0.3 | 8.0 | 12.7 | <0.0005 | 16.0 | 12.4 | 0.02 | 0.6 | 4.4 | 99.4 | 0.2 | 217 |
| Amit (B-90)[e] | 1.4 | 2.5 | 0.07 | 3.0 | 6.1 | 0.08 | 7.5 | 5.5 | 0.009 | 0.5 | 0.5 | 16.7 | 0.1 | 24 |
| Amit (B-90)[f] | 2.5 | 3.6 | 0.1 | 4.2 | 8.6 | 0.3 | 12.2 | 8.1 | 0.01 | 0.5 | 1.5 | 34.2 | 0.03 | 124 |
| | 2.4[c,d] | 4.9 | 0.09 | 6.6 | 14.8 | 0.7 | 17.3 | 12.1 | 0.005 | 0.5 | 1.6 | 80.2 | 0.1 | 95 |
| Amit (B-90)[g] | 2.4[d] | 4.8 | 0.1 | 5.9 | 15.5 | 1.8 | 17.9 | 12.4 | 0.005 | 0.5 | 1.6 | 73.5 | 0.03 | 97 |
| Amit (B-90)[h] | 3.0[d] | 5.8 | 0.2 | 4.4 | 23.3 | 5.2 | 26.4 | 15.3 | 0.006 | 0.3 | 4.1 | 67.9 | 0.07 | 52 |
| CDC ChiChi | 4.4 | 1.6 | 0.05 | 2.7 | 0.7 | 0.05 | 5.2 | 4.3 | 0.01 | 0.6 | 0.3 | 11.5 | 0.03 | 28 |
| | 2.1[c] | 1.6 | 0.007 | 3.0 | 5.0 | 0.0006 | 7.2 | 4.7 | 0.001 | 0.6 | 0.05 | 14.2 | 0.0003 | 14 |
| CDC ChiChi[g] | 1.2[d] | 1.2 | 0.03 | 0.4 | 4.2 | 1.7 | 5.4 | 3.4 | 0.006 | 0.1 | 0.2 | 1.4 | 0.01 | 0.3 |
| CDC Chico[i] | 2.5 | 1.5 | 0.09 | 1.9 | 5.4 | 0.2 | 8.0 | 3.5 | 0.01 | 0.5 | 0.7 | 6.6 | 0.01 | 21 |
| CDC Diva | 0.1 | 0.1 | 0.0002 | 0.3 | 0.9 | 0.0005 | 1.0 | 0.4 | 0.0002 | 0.7 | 0.0002 | 0.1 | <0.0001 | 0.2 |
| CDC Frontier | 1.0 | 2.1 | 0.05 | 1.0 | 6.8 | 0.1 | 7.8 | 3.2 | 0.01 | 0.3 | 0.4 | 3.3 | 0.02 | 18 |
| CDC Verano | 4.9 | 3.2 | 0.06 | 1.6 | 0.04 | 0.05 | 5.0 | 4.8 | 0.001 | 0.3 | 0.3 | 7.5 | 0.03 | 14 |
| CDC Xena | 0.05 | 0.1 | 0.0008 | 0.2 | 0.7 | 0.03 | 0.8 | 0.3 | 0.001 | 0.5 | 0.0006 | 0.1 | <0.0001 | 0.09 |
| CDC Yuma | 2.0 | 1.8 | 0.005 | 1.6 | 1.1 | 0.7 | 3.1 | 4.1 | 0.001 | 0.4 | 0.01 | 6.6 | 0.0001 | 16 |

TABLE 5-continued

Relative levels of soyasaponins from extracts of desi and kabuli chickpea, field pea and lentil exposed briefly and for 7 days to ordinary laboratory conditions.[a]

| variety[b] | S-I brief | S-I 7 day | D-I brief | D-I 7 day | S-VI brief | S-VI 7 day | total soyasaponins (D-I + S-I + S-VI ratios) brief | total soyasaponins (D-I + S-I + S-VI ratios) 7 day | D-I to soyasaponin ratio (D-I ratio/D-I + S-I + S-VI ratios) brief | D-I to soyasaponin ratio (D-I ratio/D-I + S-I + S-VI ratios) 7 day | D-I index (D-I ratio × total soyasaponin ratio) brief | D-I index (D-I ratio × total soyasaponin ratio) 7 day | D-I purity index (D-I ratio × % D-I in mixture by HPLC/ELSD peak areas) brief | D-I purity index (D-I ratio × % D-I in mixture by HPLC/ELSD peak areas) 7 day |
|---|---|---|---|---|---|---|---|---|---|---|---|---|---|---|
| Dwelley | 0.2 | 0.2 | 0.02 | 0.4 | 0.1 | 0.02 | 0.3 | 0.6 | 0.06 | 0.7 | 0.005 | 0.25 | 0.002 | 0.5 |
| Sanford | 2.0 | 0.9 | 0.2 | 1.6 | 0.2 | 0.002 | 2.4 | 2.6 | 0.07 | 0.6 | 0.4 | 4.1 | 0.1 | 5.5 |
| Sanford[e] | 0.3 | 0.1 | 0.004 | 0.2 | 0.4 | 0.0006 | 0.7 | 0.4 | 0.006 | 0.6 | 0.003 | 0.1 | 0.0002 | 0.2 |
| Sanford[g] | 0.7[d] | 0.8 | 0.02 | 0.08 | 2.1 | 1.2 | 2.8 | 2.0 | 0.007 | 0.04 | 0.05 | 0.2 | 0.004 | 0.01 |
| field pea[j] | 2.2 | 3.7 | 0.03 | 0.7 | 7.0 | 3.7 | 9.2 | 8.2 | 0.004 | 0.1 | 0.3 | 6.1 | 0.003 | 1.1 |
|  | 2.0 | 3.8 | 0.07 | 0.7 | 7.4 | 2.7 | 9.5 | 7.2 | 0.008 | 0.1 | 0.7 | 4.8 | 0.014 | 0.8 |
| lentil[k] | 1.4 | 1.9 | (0.07)[l] | 0.3 | 6.9 | 3.5 | 8.4 | 5.7 | —[m] | 0.1 | —[m] | 1.8 | —[m] | 0.4 |
|  | 1.0 | 1.8 | (0.05)[l] | 0.3 | 6.1 | 5.3 | 7.1 | 7.4 | —[m] | 0.1 | —[m] | 2.3 | —[m] | 0.4 |

[a] Crude extracts, obtained by extraction of the nondefatted flour (1 g) at room temperature with 4 ml of 80% methanol followed by centrifugation at 2000 rpm, were stored in 4 ml borosilicate glass vials (Kimble Glass Inc. Part no. 60940-4) equipped with Teflon™ lined screw-caps before treatment with Diaion HP-20 beads. The average laboratory temperature was 20.5° C. The laboratory was equipped with fluorescent lights (Sylvania SuperSaver Cool White F40CW/SS 34 watts). HPLC peak area ratios were obtained as before (see Table 1), except with a different ELSD.
[b] The nondefatted flours were obtained from the same sources as the entries of Table 1, except as designated by selected footnotes that follow.
[c] The HPLC data in these rows were derived from reanalysis of the flour samples on a different occasion than the first entry.
[d] The HPLC data in these rows are average values from duplicate flour samples.
[e] Greenhouse-grown seed.
[f] This chickpea seed sample was kindly provided in 2005 by Walker Seeds Ltd., Tisdale, SK. and ground in the laboratory with a Retsch ZM 200 centrifugal mill equipped with a 0.5 mm sieve.
[g] These samples were obtained from seeds of the Crop Development Centre (Goodale farm) harvested in 2005.
[h] This sample was obtained from seeds of the Crop Development Centre (Goodale farm) harvested in 2006.
[i] The data on CDC Chico were obtained after the original extracts in 80% methanol had been initially examined by HPLC. The HPLC samples that remained were concentrated under nitrogen and then redissolved in 80% methanol containing the internal standard before HPLC analysis.
[j] The pea flour sample, provided by Parrheim Foods (Saskatoon, SK) and analyzed in duplicate, represented a protein-rich fraction (Progress pea flour). It was a different sample than the Parrheim Progress pea sample analyzed in Table 1.
[k] The lentil seed sample (variety Laird), obtained from the Crop Development Centre (University of Saskatchewan), was ground with a Wiley mill equipped with a 40 mesh screen before duplicate analyses were carried out.
[l] The ratio obtained here was primarily for an interfering component with the same retention time as D-I (24.9 minutes). The interference showed a molecular weight of 720 Da by HPLC/MS whereas the molecular weight of D-I was 940. To calculate D-I indexes following 7-day storage, the increase in HPLC peak areas (at 24.9 minutes) was assumed to be due to elevation in levels of D-I only.
[m] Values could not be determined because of the interfering component with the same retention time as D-I.

TABLE 6

Relative concentrations of soyasaponins and yields of saponin-enriched fractions obtained from other legume crops by Diaion HP-20 bead technology following brief light exposure and 3 days of fluorescent visible light exposure of crude 80% methanol extracts in a cabinet.[a]

| variety | S-I brief | S-I 3 day | D-I brief | D-I 3 day | S-VI brief | S-VI 3 day | total soyasaponins brief | total soyasaponins 3 day | isolated yield (%) brief | isolated yield (%) 3 day | D-I/D-I + S-I + S-VI brief | D-I/D-I + S-I + S-VI 3 day | D-I index brief | D-I index 3 day |
|---|---|---|---|---|---|---|---|---|---|---|---|---|---|---|
| yellow field pea |  |  |  |  |  |  |  |  |  |  |  |  |  |  |
| CDC Mozart[b] | 0.5 | 2.5 | 0.01 | 1.4 | 3.5 | 0.7 | 4.0 | 4.6 | 0.41 | 0.37 | 0.0025 | 0.3 | 0.04 | 6.4 |
| Progress[c] | 0.8 | 1.7 | 0.04 | 1.7 | 5.6 | 0.8 | 6.4 | 4.2 | 0.71 | 0.68 | 0.006 | 0.4 | 0.3 | 7.1 |
| green field pea |  |  |  |  |  |  |  |  |  |  |  |  |  |  |
| CDC Verdi[d] | 1.4 | 5.9 | 0.01 | 0.06 | 3.9 | <0.003 | 5.3 | 5.9 | 0.43 | 0.57 | 0.002 | 0.01 | 0.05 | 0.4 |
| CDC Nitouche[e] | 2.1 | 4.1 | 0.01 | 0.08 | 3.6 | <0.003 | 5.7 | 4.2 | 0.46 | 0.54 | 0.002 | 0.02 | 0.08 | 0.3 |
| lentil |  |  |  |  |  |  |  |  |  |  |  |  |  |  |
| Eston[f] | 1.2 | 4.1 | (0.025)[g] | 0.05 | 4.8 | 1.4 | 6.0 | 5.6 | 0.51 | 0.59 | [h] | 0.004 | [h] | 0.1 |
| dry bean |  |  |  |  |  |  |  |  |  |  |  |  |  |  |
| CDC Pintium[i] | 0.1 | 0.2 | (5.4)[j] | (2.6)[k] | 1.2 | 0.3 | [h] | 1.8[l] | 0.62 | 0.53 | [h] | 0.7[l] | [h] | 2.3[l] |
| soybean |  |  |  |  |  |  |  |  |  |  |  |  |  |  |
| AC Harmony[m] | 1.4 | 3.2 | 0.3 | 4.3 | 9.5 | <0.003 | 11.2 | 7.5 | 1.09 | 1.03 | 0.03 | 0.6 | 3.8 | 32 |
| chickpea |  |  |  |  |  |  |  |  |  |  |  |  |  |  |
| Amit (B-90)[n] | 2.2 | 2.9 | 0.1 | 10.4 | 16.1 | <0.003 | 18.5 | 13.3 | 0.37 | 0.38 | 0.006 | 0.8 | 2.0 | 143 |

[a] Mature seeds were first ground in the laboratory with a Retsch ZM 200 centrifugal mill. Chloroform-defatted flour (approximately 100 g) was extracted with the original procedure described for the entries of Table 1 following brief (minimal) light exposure in the laboratory or following 3-day exposure of the crude extract (contained in a 2 liter Kimax glass Erlenmeyer flask) at 21° C. in a Controlled Environment Chamber (Hoffman Manufacturing, Inc., model SG2-22) equipped with 6 × 40 Watt fluorescent lights of the Cool White type. Using a light meter (Li-Cor Model 250 with LI-190SA quantum sensor, Lincoln, NE), readings on the laboratory benchtop and at the centre of the chamber were 6-7 and 30-32 µmol s$^{-1}$ m$^{-2}$ respectively (444-518 lux and 2220-2368 lux).
[b] This variety was harvested in 2005 from field plots of Plant Gene Resources of Canada (Saskatoon, SK).
[c] The commercial flour was obtained in May 2007 as an air-classified protein-rich fraction from Parrheim Foods (Saskatoon, SK).

TABLE 6-continued

Relative concentrations of soyasaponins and yields of saponin-enriched fractions obtained from other legume crops by Diaion HP-20 bead technology following brief light exposure and 3 days of fluorescent visible light exposure of crude 80% methanol extracts in a cabinet.[a]

| variety | S-I brief | S-I 3 day | D-I brief | D-I 3 day | S-VI brief | S-VI 3 day | total soyasaponins brief | total soyasaponins 3 day | isolated yield (%) brief | isolated yield (%) 3 day | D-I/D-I + S-I + S-VI brief | D-I/D-I + S-I + S-VI 3 day | D-I index brief | D-I index 3 day |
|---|---|---|---|---|---|---|---|---|---|---|---|---|---|---|

[d]This variety was harvested in 2005 from field plots of Plant Gene Resources of Canada (Saskatoon, SK).
[e]This sample was purchased by Agriculture and Agri-Food Canada as certified seed harvested in 2004 near Strasbourg, SK. The HPLC data in this row were average values from 2 determinations on different days with fresh solutions.
[f]These lentils were harvested in 2004 by Plant Gene Resources of Canada (Saskatoon, SK).
[g]The ratio obtained here was primarily for an interfering component (MH$^+$ 721 Da) with the same retention time as D-I (24.9 minutes). To calculate D-I indexes following 3-day exposure to light, the increase in HPLC peak areas (at 24.9 minutes) was assumed to be due to elevation in levels of D-I only.
[h]Values could not be determined because of interfering components with the same retention time as D-I.
[i]This pinto bean sample was purchased by Agriculture and Agri-Food Canada as certified seed harvested in 2005 near Outlook, SK. The HPLC data in this row were average values from 2 determinations on different days with fresh solutions.
[j]The ratio obtained here was for an interfering component (MH$^+$ 1085 Da) with the same retention time as D-I (24.9 minutes). D-I itself was not detected.
[k]From LC/MS, the peak at 24.9 minutes was represented by a mixture of the interfering component and D-I (MH$^+$ 941 Da). Light produced another component (MH$^+$ 957 Da) with a slightly shorter retention time than D-I (HPLC/ELSD peak area ratio of 1.9).
[l]Determination of these values was based on the assumption that D-I represented one-half the area counts for the peak at 24.9 minutes after light treatment.
[m]This soybean sample was harvested at field plots near Indian Head, SK. Soybean components coeluted with the internal standard. Thus, peak area for the internal standard was obtained from the mean (N = 12 or 13) of other experimental samples analyzes (in the same set) containing internal standard but without interfering components. The HPLC data in this row were average values from 2 determinations on different days with fresh solutions. Only the "B" and "E" type soyasaponins were considered.
[n]This kabuli chickpea seed sample, commercially harvested near Avonlea, SK. and included here for comparison purposes, was kindly provided in 2005 by Walker Seeds Ltd., Tisdale, SK. Reported HPLC peak area ratios for this sample were average values from 3 determinations on different days with fresh solutions.

TABLE 7

Extraction at ambient temperature of raw Amit chickpea flour (100 g) and fluorescent visible light treatment of crude alcoholic extracts.

| trial number | extraction solvent (ml) | extraction time (hours) | cabinet light (days)[a] | reduction in alcohol concentration[b] | Diaion HP-20 fraction | weight (mg) of fraction | unretained[c] | S-I | D-I | S-VI | total soyasaponins | D-I/D-I + S-I + S-VI |
|---|---|---|---|---|---|---|---|---|---|---|---|---|
| 1 | 80% MeOH (500) | 4 | 2 | evaporation | <30% MeOH | 5325[d] | 58.8 | — | — | — | — | — |
| | | | | | 30% MeOH | 557[d] | 39.6 | — | — | — | — | — |
| | | | | | 100% MeOH | 369[e] | 4.6[f] | 3.5 | 7.0 | — | 10.5 | 0.7 |
| 2 | 80% MeOH (500) | 4 | 2 | dilution | <30% MeOH | 7332[d] | 32.5 | — | — | — | — | — |
| | | | | | 30% MeOH | 80[d] | 36.3 | — | — | — | — | — |
| | | | | | 100% MeOH | 282 | 1.0[f] | 4.1 | 8.1 | 0.3 | 12.5 | 0.6 |
| 3 | 60% EtOH (500) | 4 | 3 | evaporation | <30% EtOH | 7798[d] | 66.0 | — | — | — | — | — |
| | | | | | 30% EtOH | 605[d] | 69.5 | — | — | — | — | — |
| | | | | | 100% EtOH | 379[g,h] | 4.3[f] | 5.9 | 7.1 | — | 13.0 | 0.5 |
| 4 | 60% EtOH (500) | 4 | 3 | dilution | <30% EtOH | 8409[d] | 65.4[f] | — | — | — | — | — |
| | | | | | 30% EtOH | 193[d] | 59.7[f] | — | — | — | — | — |
| | | | | | 100% EtOH | 351[h] | 2.3[f] | 6.8 | 8.2 | — | 15.0 | 0.5 |

[a]The cabinet was a Controlled Environment Chamber (Hoffman Manufacturing, Inc., model SG2-22) equipped with 6 × 40 Watt fluorescent lights of the Cool White type and maintained at 21° C. The Amit chickpea sample was kindly provided in 2005 by Walker Seeds Ltd., Tisdale, SK.
[b]After light treatment, the alcohol concentration of the crude extract was reduced to approximately 25% either by rotary evaporation (bath temperature 26° C. for MeOH; 32° C. for EtOH) or by dilution with water (1000 ml) before addition of the HP-20 beads. Beads were added with the use of water (approximately 200 ml in trials 1 and 3) and stirred overnight (16-18 hours) before filtration and subsequent 2-hour washes (magnetic stirring) with 30% alcohol (500 ml) and 100% alcohol (500 ml).
[c]The unretained peak of unknown identity eluted at 2 minutes.
[d]These samples were obtained by rotary evaporation and freeze-drying.
[e]A portion of this sample (150 mg), dissolved in 80% methanol at 10 mg/ml, was purified by medium pressure LC (AKTAExplorer 100 LC system from Amersham Biosciences Inc.) with a 24 ml (10 × 300 mm) reversed phase column custom packed with 15 μm styrene/divinylbenzene beads (Source ™ 15RPC Tricorn ™10/300 GL, supplied by GE Healthcare Bio-Sciences AB, Uppsala, Sweden). Eluent A (10 mM ammonium hydroxide) and B (5 mM ammonium hydroxide in 50% acetonitrile) were the same as with the previous purifications with a 3 ml Resource column (see Table 2). Initial conditions were 90% A and 10% B (5% acetonitrile) for 4 minutes, followed by a linear gradient from 10% B to 39% B over 51 minutes and a more shallow gradient to 44% B over 33.6 minutes. Thereafter, a sharp gradient was performed from 44% B to 100% B over 19.2 minutes. This gradient was maintained for 7.9 minutes before recycling to the initial conditions. The flow rate was 6 ml/min. Samples (3 × 50 ml) were injected (5 ml) with a Superloop (Amersham Biosciences). Fractions (3 ml) were combined as appropriate and bubbled with nitrogen gas before Savant evaporation at 43° C. S-I (4.38 mg) and D-I (7.78 mg; 0.019% yield) of high purity by HPLC/ELSD were obtained.
[f]HPLC peak area ratios in these rows are average values from 2-4 determinations. Purity/D-I indexes (calculated according to Table 5) for the 100% alcohol fractions of trials 1-4 were 314/84, 413/105, 248/95 and 369/124 respectively.
[g]This sample (150 mg) was purified as described in footnote[e], giving impure S-I (7.74 mg) and D-I (7.59 mg; 0.019% yield) of high purity by HPLC/ELSD.
[h]These samples were not completely dry.

TABLE 8

Properties of the saponin-enriched fractions of Amit chickpea flours extracted with 60% ethanol and diluted with water before addition of Dinion HP-20 beads.[a]

| seed source | S-I brief | S-I 3 day | D-I brief | D-I 3 day | S-VI brief | S-VI 3 day | total soyasaponins brief | total soyasaponins 3 day | isolated yield (%)[b] brief | isolated yield (%)[b] 3 day | D-I/D-I + S-I + S-VI brief | D-I/D-I + S-I + S-VI 3 day | D-I index brief | D-I index 3 day |
|---|---|---|---|---|---|---|---|---|---|---|---|---|---|---|
| Walker 2005[c] | 8.0 | 7.5 | 0.5 | 8.5 | 1.9 | <0.003 | 10.4 | 16.0 | 0.274 | 0.266 | 0.05 | 0.5 | 5.5 | 138 |
| Goodale 2005[d] | 7.9 | 8.3 | 0.6 | 4.7 | 5.0 | <0.003 | 13.6 | 13.0 | 0.255 | 0.269 | 0.05 | 0.4 | 8.2 | 62 |
| Goodale 2006[d] | 8.4 | 12.5 | 0.5 | 6.2 | 2.5 | <0.003 | 11.4 | 18.6 | 0.339 | 0.322 | 0.04 | 0.3 | 5.9 | 115 |

[a]Raw flour (100 g) from the Retsch mill was used. The mixture was stirred at room temperature for 4 hours in 60% ethanol (500 ml) and filtered. The filtrate was either exposed briefly to laboratory light or to 3 days of light in a Controlled Environment Chamber (Hoffman Manufacturing, Inc., model SG2-22) equipped with 6 × 40 Watt fluorescent lights of the Cool White type. Using a light meter (Li-Cor Model 250 with LI-190SA quantum sensor, Lincoln, NE), readings on the laboratory benchtop and at the centre of the chamber were 6-7 and 30-32 $\mu mol\ s^{-1}\ m^{-2}$ respectively (444-518 lux and 2220-2368 lux). After dilution of the crude extract with water (1000 ml), the <30% ethanol and 30% ethanol washes from the Diaion HP-20 beads were obtained (and discarded) before washing the beads with 100% ethanol (see Table 7). HPLC peak area ratios were average values from 2 determinations on different days with fresh solutions.
[b]Based on the dry mass of the Diaion HP-20 100% ethanol fraction.
[c]The seeds were supplied in 2005 by Walker Seeds Ltd. (Tisdale, SK). This experiment (with the 3 day light exposure) can be considered as a repeat of trial 4 (Table 7), except only the Diaion HP-20 EtOH fraction was isolated.
[d]These seeds were harvested in 2005 and 2006 at the Goodale farm of the Crop Development Centre, University of Saskatchewan.

TABLE 9

Comparison of the distribution of saponins isolated from Amit chickpea flour in two solvent systems with three photoreactor light sources and sunlight.[a]

| light source | S-I MeOH | S-I EtOH | D-I MeOH | D-I EtOH | S-VI MeOH | S-VI EtOH | total soyasaponins MeOH | total soyasaponins EtOH | isolated yield (%)[b] MeOH | isolated yield (%)[b] EtOH | D-I/D-I + S-I + S-VI MeOH | D-I/D-I + S-I + S-VI EtOH | D-I index MeOH | D-I index EtOH |
|---|---|---|---|---|---|---|---|---|---|---|---|---|---|---|
| Cool White[c] | 7.8 | 12.3 | 8.7 | 3.5 | <0.003 | 0.02 | 16.5 | 15.8 | 0.263 | 0.234 | 0.5 | 0.2 | 144 | 56 |
| | | 11.1 | | 3.7 | | <0.003 | | 14.7 | | 0.290 | | 0.2 | | 61 |
| UVA[d] | 10.8 | 12.5 | 4.2 | 2.4 | <0.003 | <0.003 | 15.0 | 14.9 | 0.258 | 0.272 | 0.3 | 0.2 | 64 | 35 |
| UVC[e] | 6.7 | 7.3 | 7.8 | 6.1 | <0.003 | 0.006 | 14.5 | 13.4 | 0.261 | 0.299 | 0.5 | 0.5 | 114 | 84 |
| Sunlight[f] | 7.3 | 11.1 | 9.0 | 3.6 | <0.003 | <0.003 | 16.3 | 14.7 | 0.274 | 0.284 | 0.6 | 0.2 | 146 | 53 |

[a]Amit seeds were supplied in 2005 by Walker Seeds Ltd. (Tisdale, SK). Approximately 100 g of raw flour from the Retsch mill was used. The mixture was stirred at room temperature for 4 hours in 80% methanol or 60% ethanol (500 ml) and filtered. The filtrate, contained in a 500 ml Erlenmeyer flask (Pyrex glass type), was exposed to light at ambient temperature for 2 (MeOH) or 3 (EtOH) days in a photoreactor (Model LZC-ORG, Luzchem Research, Inc., Ottawa, ON) containing 10 fluorescent tubes (12 inch length, side mounted) or at an outside Saskatoon location exposed to sunlight. After dilution of the crude extract with water (1000 ml), the <30% alcohol and 30% alcohol washes from the Diaion HP-20 beads were obtained (discarded) before washing the beads with 100% alcohol. HPLC peak area ratios were average values from 2 determinations on different days with fresh solutions.
[b]Based on the dry mass of the Diaion HP-20 100% alcohol fraction.
[c]Sylvania T5 tube (8 watts). Using a light meter (Li-Cor Model 250 with LI-190SA quantum sensor, Lincoln, NE), the reading at the centre of the photoreactor was 132-144 $\mu mol\ s^{-1}\ m^{-2}$ (9,768-10,656 lux). The experiments with ethanol were done twice.
[d]Wavelength centered at 350 nm (Hitachi FL8BL-B).
[e]Germicidal lamps with a strong emission at 254 nm (Ushio G8T5).
[f]The experiment with ethanol was illuminated in 2007 on July 14 (mostly cloudy, high of 29° C.), 15 (mostly sunny, 26° C.) and 16 (mostly cloudy, 27° C.) whereas illumination in methanol occurred under mostly cloudy conditions on September 1 (18.5° C.) and 2 (21° C.). Overcast to very bright summer days vary from approximately 30,000-100,000 lux.

TABLE 10

Experiments on mixing fractions isolated from Amit chickpea extracts and illuminating the mixtures dissolved in 80% methanol to fluorescent visible light.

| trial no. | solvent | source of fractions | target ratio | 100% MeOH | 30% MeOH | <30% MeOH | CHCl$_3$ | days of light | unretained | S-I | D-I | S-VI | total soyasaponins | D-I/D-I + S-I + S-VI |
|---|---|---|---|---|---|---|---|---|---|---|---|---|---|---|
| 1 | 80% MeOH | prep A[a] | 3:0 | 3.09 | — | — | — | 2 | 4.4 | 11.0 | 1.1 | 0.8 | 12.8 | 0.09 |
| | | | 3:0 | 2.92 | — | — | — | 2 | 3.8 | 8.9 | 0.9 | 0.5 | 10.4 | 0.09 |
| | | | 3:1.5 | 2.99 | — | 1.64[b] | — | 2 | 54.1 | 7.0 | 1.0 | 0.1 | 8.2 | 0.1 |
| | | | 3:4.5 | 2.99 | — | 4.54[b] | — | 2 | 112.4 | 10.4 | 1.9 | 0.2 | 12.5 | 0.1 |
| | | | 3:1.5 | 2.97 | 1.78[b] | — | — | 2 | 25.9 | 9.6 | 1.4 | 0.3 | 11.3 | 0.1 |
| | | | 3:4.5 | 2.99 | 4.62[b] | — | — | 2 | 93.9 | 7.9 | 1.4 | — | 9.3 | 0.1 |
| | | | 3:1.5 | 2.93 | — | — | 1.40[b] | 2 | 3.1 | 7.3 | 0.6 | 0.3 | 8.2 | 0.08 |
| | | | 3:4.5 | 2.94 | — | — | 4.82[b] | 2 | 4.3 | 11.2 | 0.9 | 0.9 | 13.1 | 0.07 |
| 2 | 80% MeOH | prep B[c] | 3:0 | 3.14 | — | — | — | 2 | 2.6 | 7.7 | 1.9 | 1.0 | 10.7 | 0.2 |
| | | | 3:0 | 3.13 | — | — | — | 2 | 2.8 | 8.5 | 2.1 | 1.2 | 11.8 | 0.2 |
| | | | 3:1.5 | 2.92 | — | 1.57 | — | 2 | 26.8 | 7.8 | 3.9 | 0.2 | 11.9 | 0.3 |

TABLE 10-continued

Experiments on mixing fractions isolated from Amit chickpea extracts and illuminating the mixtures dissolved in 80% methanol to fluorescent visible light.

| trial no. | solvent | source of fractions | target ratio | mass (mg) added to reaction vial | | | | days of light | HPLC/ELSD, component peak area to internal standard ratio | | | | | |
|---|---|---|---|---|---|---|---|---|---|---|---|---|---|---|
| | | | | 100% MeOH | 30% MeOH | <30% MeOH | CHCl$_3$ | | unretained | S-I | D-I | S-VI | total soyasaponins | D-I/D-I + S-I + S-VI |
| | | | 3:4.5 | 3.06 | — | 4.49 | — | 2 | 72.8 | 5.9 | 3.4 | — | 9.3 | 0.4 |
| | | | 3:1.5 | 3.07 | 1.52 | — | — | 2 | 26.2 | 8.4 | 3.7 | 0.4 | 12.5 | 0.3 |
| | | | 3:4.5 | 3.06 | 4.48 | — | — | 2 | 77.3 | 6.9 | 4.4 | — | 11.3 | 0.4 |
| | | | 3:1.5 | 3.07 | — | — | 1.83$^d$ | 2 | 3.2 | 11.1 | 2.1 | 1.7 | 14.9 | 0.1 |
| | | | 3:4.5 | 2.98 | — | — | 4.43$^d$ | 2 | 2.6 | 6.1 | 1.3 | 1.7 | 9.1 | 0.1 |
| | | | | 2.94$^e$ | — | — | — | 0 | 2.1 | 5.8 | 0.5 | 2.8 | 9.1 | 0.06 |
| 3 | 80% MeOH | prep E$^f$ | 3:0 | 3.04 | — | — | — | 2 | 4.5 | 6.1 | 1.7 | 1.4 | 9.2 | 0.2 |
| | | | 3:0 | 3.06 | — | — | — | 2 | 5.3 | 6.9 | 1.9 | 1.6 | 10.4 | 0.2 |
| | | | 3:1.5 | 2.96 | — | 1.52 | — | 2 | 25.7 | 5.4 | 2.9 | 0.3 | 8.6 | 0.3 |
| | | | 3:4.5 | 3.03 | — | 4.41 | — | 2 | 65.4 | 5.7 | 3.5 | 0.03 | 9.3 | 0.4 |
| | | | 3:1.5 | 3.01 | 1.63 | — | — | 2 | 27.7 | 6.4 | 3.5 | 0.4 | 10.3 | 0.3 |
| | | | 3:4.5 | 3.01 | 4.64 | — | — | 2 | 72.9 | 6.4 | 4.8 | 0.001 | 11.2 | 0.4 |
| | | | 3:1.5 | 2.96 | — | — | 1.47 | 2 | 4.2 | 6.0 | 1.4 | 2.0 | 9.5 | 0.2 |
| | | | 3:4.5 | 3.00 | — | — | 4.58 | 2 | 4.4 | 6.9 | 1.5 | 1.7 | 10.2 | 0.1 |
| | | | | 3.01$^e$ | — | — | — | 0 | 4.1 | 4.4 | 0.2 | 5.9 | 10.5 | 0.02 |
| | | | | 3.07$^g$ | — | — | — | 0 | 3.7 | 4.8 | 0.3 | 4.2 | 9.3 | 0.03 |

The experiments of Table 10 were conducted by transferring the appropriate Diaion HP-20 fractions to borosilicate glass vials (Kimble 60940-4) and adding 80% methanol (4 ml). After vortexing, the vials were stored for 2 days at 21° C. in a Controlled Environment Chamber (Hoffman Manufacturing, Inc., model SG2-22) equipped with 6 × 40 Watt fluorescent lights of the Cool White type. The mixtures were evaporated to dryness with an N-Evap and Savant apparatus. On the day of analysis, the samples were redissolved in 80% methanol (3 ml) containing α-hederin (0.25 mg/ml) and syringe filtered (0.45 μm) into glass inserts of HPLC autosampler vials.
$^a$The 100% MeOH fraction, stored in a refrigerator for a year, was prepared from the flour of commercial Amit chickpeas (Walker Seeds Ltd., Tisdale, SK) using the conventional procedure with chloroform defatting, hot 80% methanol (2 l) as extraction solvent with brief exposure to light and Diaion HP-20 beads.
$^b$These fractions were isolated in an experiment after light treatment (trial 1 of Table 7).
$^c$All fractions were derived from the flour described in footnote $^a$ using the same techniques with minimal (brief) exposure to light. The fractions had been stored in a refrigerator at 5° C. for 2 weeks before use in this experiment.
$^d$The chloroform fraction was from the same source as in trial 1.
$^e$These reference samples were stored in solution for 2 days (−18° C., protected from light) before evaporation and HPLC analysis.
$^f$Prep E was conducted in the same manner as prep B except the Diaion HP-20 mixtures were stirred in the dark and the freeze-drying flasks for obtaining the <30% MeOH and 30% MeOH fractions were wrapped in Al foil. Fractions from prep E had been stored in a refrigerator at 5° C. for 4 days before use. Experiments with 1 g and 0.2 g of the raw flour of commercial Amit chickpeas (Walker Seeds Ltd., Tisdale, SK) were also performed during trial 3. The flour samples were extracted at room temperature with 80% methanol (4 ml) during 1 hour. After centrifugation, the supernatant was placed in the light cabinet for 2 days then evaporated by N-Evap and Savant apparatus. The residues that remained (ca. 62 and 23 mg) were redissolved in 80% methanol (3 ml) containing α-hederin (0.25 mg/ml) and syringe filtered (0.45 μm) before HPLC analysis along with the other experimental samples. The D-I/D-I + S-I + S-VI ratios from HPLC were 0.7 (1 g) and 0.8 (0.2 g). Flour extracts prepared without light exposure (Al foil wrapped tubes) or by quick extraction and evaporation, the D-I/D-I + S-I + S-VI ratios were <0.01.
$^g$This reference sample was dissolved with brief vortexing in 80% methanol then the solvent was removed (N-Evap) and the residue stored in the dark until HPLC analysis in 80% methanol containing 0.25 mg/ml of α-hederin.

TABLE 11

Mixture tests with Amit chickpea extracts and potential photosensitizers with exposure in 80% methanol to fluorescent visible light.

| test no. | additions to reaction vial | | | | | | days of light | HPLC/ELSD, component peak area to internal standard ratio | | | | | |
|---|---|---|---|---|---|---|---|---|---|---|---|---|---|
| | 100% MeOH$^a$ (mg) | 30% MeOH$^a$ (mg) | riboflavin$^b$ (μM) | FMN$^c$ (μM) | FAD$^d$ (μM) | bergapten$^e$ (μM) | | unretained | S-I | D-I | S-VI | total soyasaponins | D-I/D-I + S-I + S-VI |
| 1 | 2.96 | — | — | — | — | — | 2 | 3.9 | 5.4 | 0.9 | 0.9 | 7.2 | 0.1 |
| 2 | 2.99 | 1.47 | — | — | — | — | 2 | 24.3 | 7.0 | 2.4 | 0.3 | 9.7 | 0.2 |
| 3 | 3.01 | 4.63 | — | — | — | — | 2 | 70.9 | 7.3 | 3.5 | <0.003 | 10.8 | 0.3 |
| 4 | 3.02 | 7.58 | — | — | — | — | 2 | 106 | 6.0 | 3.5 | <0.003 | 9.5 | 0.4 |
| 5 | 3.00 | — | 10 | — | — | — | 2 | 4.7 | 8.5 | 4.0 | <0.003 | 12.4 | 0.3 |
| 6 | 2.95 | — | 50 | — | — | — | 2 | 4.5 | 5.8 | 3.0 | <0.003 | 8.8 | 0.3 |
| 7 | 2.96 | — | 100 | — | — | — | 2 | 4.8 | 4.7 | 2.6 | <0.003 | 7.4 | 0.4 |
| 8 | 2.96 | — | — | 10 | — | — | 2 | 4.8 | 6.5 | 3.3 | <0.003 | 9.9 | 0.3 |
| 9 | 3.03 | — | — | 50 | — | — | 2 | 5.1 | 4.5 | 2.9 | <0.003 | 7.4 | 0.4 |
| 10 | 2.99 | — | — | 100 | — | — | 2 | 6.5 | 0.3$^f$ | 1.8 | <0.003 | 2.1 | 0.5 |
| 11 | 3.05 | — | — | — | 10 | — | 2 | 5.1 | 6.8 | 3.3 | <0.003 | 10.1 | 0.3 |
| 12 | 2.97 | — | — | — | 50 | — | 2 | 5.6 | 5.5 | 3.0 | <0.003 | 8.6 | 0.4 |
| 13 | 2.98 | — | — | — | 100 | — | 2 | 6.9 | 4.0 | 2.8 | <0.003 | 6.7 | 0.4 |
| 14 | 3.00 | — | — | — | — | 10 | 2 | 4.8 | 8.2 | 1.6 | 1.2 | 11.0 | 0.1 |
| 15 | 2.96 | — | — | — | — | 50 | 2 | 3.8 | 6.0 | 1.2 | 1.2 | 8.4 | 0.1 |
| 16 | 3.06 | — | — | — | — | 100 | 2 | 4.4 | 8.0 | 1.7 | 1.4 | 11.1 | 0.2 |
| 17 | 2.98 | 4.47 | 50 | — | — | — | 2 | 75.5 | 7.5 | 2.6 | <0.003 | 10.0 | 0.3 |
| 18 | 2.98 | 4.58 | — | — | — | 50 | 2 | 70.7 | 7.4 | 3.6 | <0.003 | 11.0 | 0.3 |
| 19 | 2.99 | 4.48 | 50 | — | — | 50 | 2 | 67.1 | 7.8 | 3.1 | <0.003 | 10.9 | 0.3 |

TABLE 11-continued

Mixture tests with Amit chickpea extracts and potential photosensitizers with exposure in 80% methanol to fluorescent visible light.

| | additions to reaction vial | | | | | | HPLC/ELSD, component peak area to internal standard ratio | | | | | |
|---|---|---|---|---|---|---|---|---|---|---|---|---|
| | 100% | 30% | | | | | days | | | | | |
| test no. | MeOH[a] (mg) | MeOH[a] (mg) | riboflavin[b] (μM) | FMN[c] (μM) | FAD[d] (μM) | bergapten[e] (μM) | of light | unretained | S-I | D-I | S-VI | total soyasaponins | D-I/D-I + S-I + S-VI |
| 20 | 3.06[g] | — | — | — | — | — | 0 | 3.7 | 5.6 | 0.3 | 3.8 | 9.7 | 0.03 |
| 21 | 2.98[h] | — | — | — | — | — | 0 | 3.7 | 5.4 | 0.3 | 4.9 | 10.6 | 0.03 |

The tests of Table 11 were conducted in 80% methanol (4 ml) by transferring the appropriate Diaion HP-20 fractions or stock solutions (also in 80% methanol) of potential commercial photosensitizers to borosilicate glass vials (Kimble 60940-4). After vortexing, the vials were stored for 2 days at 21° C. in a Controlled Environment Chamber (Hoffman Manufacturing, Inc., model SG2-22) equipped with 6 x 40 Watt fluorescent lights of the Cool White type. The mixtures were evaporated to dryness with an N-Evap and Savant apparatus. On the day of analysis, the samples were redissolved in 80% methanol (3 ml) containing α-hederin (0.25 mg/ml) and syringe filtered (0.45 μm) into glass inserts of HPLC autosampler vials.
[a]These fractions, taken from prep E (Table 10), had been stored in a refrigerator at 5° C. for 2 months before use.
[b](-)-Riboflavin (Sigma R4500).
[c]Riboflavin 5' phosphate sodium salt hydrate (Sigma R7774).
[d]Flavin adenine dinucleotide disodium salt hydrate (Sigma F6625).
[e]5-Methoxypsoralen (Sigma 275727).
[f]A number of additional peaks were observed with short retention times of 12-20 minutes.
[g]This reference sample was stored in solution for 2 days (−18° C., protected from light) before evaporation and HPLC analysis.
[h]This reference sample was dissolved with brief vortexing in 80% methanol then the solvent was removed (N-Evap) and the residue stored in the dark until HPLC analysis in 80% methanol containing 0.25 mg/ml of α-hederin.

TABLE 12

Soyasaponin distribution in crude extracts of four legume flours (1 g) extracted with 80% methanol and treated for 48 hours with fluorescent visible light in the presence of three concentrations of added riboflavin.

| | riboflavin added | HPLC/ELSD, component peak area to internal standard ratio | | | | |
|---|---|---|---|---|---|---|
| flour type | (μM) | S-I | D-I | S-VI | total soyasaponins | D-I/D-I + S-I + S-VI |
| CDC Desiray chickpea | 1 | 2.1 | 4.0 | <0.003 | 6.0 | 0.7 |
| | 10 | 2.2 | 3.0 | <0.003 | 5.2 | 0.6 |
| | 50 | 3.2 | 3.0 | <0.003 | 6.1 | 0.5 |
| CDC Frontier chickpea | 1 | 3.7 | 8.9 | <0.003 | 12.7 | 0.7 |
| | 10 | 6.7 | 7.3 | <0.003 | 14.1 | 0.5 |
| | 50 | 8.4 | 6.5 | <0.003 | 14.8 | 0.4 |
| CDC Verdi green pea | 1 | 8.9 | 0.8 | <0.003 | 9.7 | 0.08 |
| | 10 | 5.4 | 2.2 | <0.003 | 7.6 | 0.3 |
| | 50 | 4.9 | 2.2 | <0.003 | 7.1 | 0.3 |
| CDC Nitouche green pea | 1 | 7.9 | 2.2 | <0.003 | 10.1 | 0.2 |
| | 10 | 4.2 | 3.0 | <0.003 | 7.2 | 0.4 |
| | 50 | 5.1 | 3.2 | <0.003 | 8.3 | 0.4 |

Raw flour samples, described in Tables 5 and 6, were extracted at room temperature with 4 ml of 80% methanol (containing 1, 10 or 50 μM riboflavin) during 1 hour. After centrifugation, the supernatant was placed at 21° C. for 48 hours in a Controlled Environment Chamber (Hoffman Manufacturing, Inc., model SG2-22) equipped with 6 x 40 Watt fluorescent lights of the Cool White type then evaporated by N-Evap and Savant apparatus. The residues that remained were redissolved in 80% methanol (3 ml) containing α-hederin (0.25 mg/ml) and syringe filtered (0.45 μm) before HPLC analysis.

TABLE 13

Detection of additional chickpea components in seed and leaf extracts by electrospray LC/MS.[a]

| | MH+ of minor saponins | | | | MH+ of other components[b] | | | | | | MH+ of unknowns-retention time in minutes[c] | | | |
|---|---|---|---|---|---|---|---|---|---|---|---|---|---|---|
| | | 1252 | 1268 | | | | | | | | | | | |
| | 797 S-III[d] | 941 D-I[e] | 22-gr S-I[f] | 22-gg S-I[f] | 125 2-bf[f] | 133 4,5-df[f] | 447 sissotrin | 533 6-mf[f] | 581 kag[f] | 667 kamg[f] | | | | |
| desi seed extracts[g] | 25.7[h] | 27.8 | 16.1 | 14.8 | 12.0 | 22.5 | 18.0 | 19.6 | 22.6 | 42.2 | 205-7.7[h] | 312-5.2[i] | 958-18.9 | 1086-22.7 |
| | | | | | | | | | | | 217-10.5 | 493-9.9 | 1030-23.1 | 1099-25.5 |
| | | | | | | | | | | | 247-9.8 | 805-18.8 | 1043-30.0 | 1106-22.5 |
| | | | | | | | | | | | 295-10.1 | 807-17.1 | 1084-22.5 | 1238-15.4 |

TABLE 13-continued

Detection of additional chickpea components in seed and leaf extracts by electrospray LC/MS.[a]

| | MH+ of minor saponins | | | | MH+ of other components[b] | | | | | | MH+ of unknowns-retention time in minutes[c] | | | |
|---|---|---|---|---|---|---|---|---|---|---|---|---|---|---|
| | | | 1252 | 1268 | | | | | | | | | | |
| | 797 S-III[d] | 941 D-I[e] | 22-gr S-V[f] | 22-gg S-V[f] | 125 2-bf[f] | 133 4,5-df[f] | 447 sissotrin | 533 6-mt[f] | 581 kag[f] | 667 kamg[f] | | | | |
| kabuli seed extracts[j] | 25.7 | 27.8 | 16.1 | 14.8 | 12.0 | 22.5 | 18.0 | 19.6 | 22.6 | 42.2 | 205-7.7 217-10.5 247-9.8 295-10.1 | 312-5.2[i] 493-9.9 805-18.8 807-17.1 | 958-18.9 1030-23.1 1043-30.0 1084-22.5 | 1086-22.7 1099-25.5 1106-22.5 1238-15.4 |
| green leaf[k] | | | | | | | 18.0 | 19.6 | | | 205-7.7 217-10.5 247-9.8 | | | |
| dry leaf[l] | | [m] | | | | | 18.0 | 19.6 | | | 205-7.7 217-10.5 247-9.8 | | | |

[a]Diaion HP-20 methanol fractions were analyzed on a Quattro LC mass spectrometer after injection of 10 μl of a 4-8 mg/ml solution of the mixtures in 80% methanol.
[b]These components correspond in molecular mass to chickpea components described in the literature. Although ions at m/z 125, 133 and 667 were usually found in the indicated extracts, the concentrations were low and collision-induced dissociation experiments from LC/MS gave insufficient evidence to support their identity (see FIG. 8).
[c]The molecular masses of the 16 minor components listed here had not previously been reported as components of the chickpea.
[d]See FIG. 8 for structures and abbreviations of the chemicals indicated in this row. The structure of D-I was given in FIG. 1.
[e]Detection of D-I signified that S-I (MH+ 943, retention time 24.3 min) and S-VI (MH+ 1069, retention time 28.7 min) were also present in the same extracts (see also Table 1).
[f]Since authentic reference samples were unavailable, the identity of these components should be considered tentative.
[g]The indicated components were found in each desi extract (see Table 1 for the source) except that the extract from CDC Nika did not show an ion at m/z 125.
[h]The retention times (in minutes) were those from LC/MS. If the retention time is not shown in the table, the component was not found in the extract by LC/MS.
[i]This component, although giving weak ion chromatograms with m/z 312, might be biochanin C, an unidentified compound previously isolated from the chickpea and claimed to have a molecular mass of 311 Da.
[j]The indicated components were found in each kabuli extract (see Table 1) except the ions at m/z 125 and 1043 were absent in CDC Frontier and the ions at m/z 133 and 1043 were absent in greenhouse-grown Amit and Sanford seed. The extract from greenhouse-grown Sanford also lacked the ion at m/z 1238. The extract from CDC Verano did not show ions at m/z 805 and 807.
[k]This extract was obtained from the green leaves of desi chickpea (an unspecified variety) growing in a greenhouse. The leaves were freeze-dried and then ground with a Wiley mill equipped with a 40 mesh screen. The resulting green powder (55 g), after defatting with chloroform, was extracted with refluxing 80% methanol and the HP-20 MeOH fraction was obtained (1.12 g of a dark brown viscous oil) following minimal (brief) light exposure as described in the conventional method with chickpea flour [Table 1 and paragraph 0059].
[l]This extract was obtained from the dry leaves of desi chickpea grown to maturity in a 2002 field plot located at the Research Centre (Saskatoon, SK). After removing the stems and pods, the leaves were processed as described for the green leaf experiment. The HP-20 MeOH material (3.38 g) was isolated as a dark brown semi-solid.
[m]There appeared to be a trace of S-I (and S-VI) in this extract.

TABLE 14

Detection by electrospray LC/MS of chickpea components in aqueous alcohol washes from crude seed and leaf extracts adsorbed onto Diaion HP-20 beads.

| source of crude extract | solvent | cabinet light (days) | Diaion HP-20 fraction | MH+ of detected component | | | | | |
|---|---|---|---|---|---|---|---|---|---|
| | | | | 205 | 217 | 247 | 295 | 312 | 493 |
| prep E Table 10 | MeOH | 0 | <30% MeOH | ++[a] | +[a] | ++ | ++ | + | + |
| | | | 30% MeOH | +++[a] | + | ++ | +++ | + | + |
| prep D example 6 | EtOH | 0 | <30% EtOH | + | + | ++ | +++ | + | + |
| | | | 30% EtOH | ++ | + | ++ | ++ | + | + |
| trial 1 Table 7 | MeOH | 2 | <30% MeOH | ++ | + | ++ | ++ | + | + |
| | | | 30% MeOH | +++ | + | +++ | +++ | + | + |
| trial 2 Table 7 | MeOH | 2 | <30% MeOH | ++ | + | ++ | ++ | + | + |
| | | | 30% MeOH | +++ | + | +++ | ++ | + | + |
| trial 3 Table 7 | EtOH | 3 | <30% EtOH | ++ | + | ++ | ++ | + | + |
| | | | 30% EtOH | +++ | + | ++ | ++ | + | + |
| trial 4 Table 7 | EtOH | 3 | <30% EtOH | ++ | + | ++ | ++ | + | + |
| | | | 30% EtOH | +++ | + | ++ | ++ | + | + |
| green leaf Table 13 | MeOH | 0 | 30% MeOH | ++ | ++ | + | nd | nd | nd |

TABLE 14-continued

Detection by electrospray LC/MS of chickpea components in aqueous alcohol washes from crude seed and leaf extracts adsorbed onto Diaion HP-20 beads.

| source of crude extract | solvent | cabinet light (days) | Diaion HP-20 fraction | \multicolumn{6}{c}{$MH^+$ of detected component} | | | | | |
|---|---|---|---|---|---|---|---|---|---|
| | | | | 205 | 217 | 247 | 295 | 312 | 493 |
| dry leaf Table 13 | MeOH | 0 | 30% MeOH | +++ | ++ | + | + | nd | nd |

[a]Relative height of signal response from positive ion electrospray traces obtained during LC/MS.
Nd, not detected.

What is claimed is:

1. A method of producing a plant composition comprising dehydrosoyasaponin I (D-I), the method comprising,
   a) extracting a plant flour comprising soyasaponin VI (S-VI) with a soyasaponin extracting solvent to produce an extract, and;
   b) treating the extract with light in an amount between about 500 lux and about 8000 lux.

2. The method of claim 1, wherein said extracting further comprises, or is preceded by a step of processing a plant or part thereof to produce a flour.

3. The method of claim 1, further comprising one or more steps of purifying dehydrosoyasaponin I (D-I) from the extract treated with light.

4. The method of claim 1, wherein the plant flour comprises flour derived from a legume.

5. The method of claim 1, wherein the plant flour comprises seed flour.

6. The method of claim I, wherein the step of extracting and treating are performed concurrently.

7. The method of claim 1, wherein the soyasaponin extracting solvent is an aqueous alcohol solvent.

8. The method of claim 7, wherein the aqueous alcohol solvent comprises ethanol and water or methanol and water.

9. The method of claim 8, wherein the aqueous alcohol solvent comprises between about 10:90 alcohol:water and about 90:10 alcohol:water (by volume).

10. The method of claim 1, wherein said treating comprises illumination with light for a period of from about 1 day to about 7 days.

11. The method of claim 10 wherein said light is in the visible range and in an amount between about 2000 and 2500 lux.

12. The method of claim 1, wherein the plant flour is derived from one or more of soybeans (*Glycine max*), field pea (*Pisum sativum*), chickpea (*Cicer arietinum*), lentil {*Lens culinaris*}, alfalfa (*Medicago sativa*), American groundnut (*Apios americana*), scarlet runner beans (*Phaseolus coccineus*), blue or narrow leafed lupin (*Lupinus angustifolius*), hyacinth bean (*Dolichos lablab*), black bean (*Vigna mungo*), adzuki or azuki bean (*Vigna angularis*, synonymous with *Phaseolus angularis*), one or more *Desmodium* species, *Wistaria brachybotrys, Sophora subprostrata, Lupinus polyphyllus, Lupinus arboreus, Trifolium alexandrinum, Abrus cantoniensis,* or *Phaseolus vulgaris*.

13. The method of claim 12, wherein the plant flour is from chickpea seed.

14. The method of claim 13, wherein the chickpea seed is Amit.

15. The method of claim 2 wherein the step of processing comprises grinding, milling, pulverizing, crushing, pressing, or pounding the plant or part thereof to produce a flour that comprises a meal or powder.

16. The method of claim 1, comprising
   a) extracting a legume plant flour comprising soyasaponin VI (S-VI) with a aqueous alcohol soyasaponin extracting solvent to produce an extract, and;
   b) treating the extract with visible light at an intensity of 2000 to 2500 lux for a period of time greater than about 1 hour.

17. The method of claim 1, wherein the plant flour comprises fermented seed or fermented seed flour.

18. The method of claim 1 wherein the soyasaponin extracting solvent comprises water and the step of extracting employs subcritical water extraction.

* * * * *